United States Patent [19]
Bohlmann et al.

[11] Patent Number: 5,807,899
[45] Date of Patent: Sep. 15, 1998

[54] TRIPHENYLETHYLENES, PROCESS FOR THEIR PRODUCTION, PHARMACEUTICAL PREPARATIONS THAT CONTAIN THESE TRIPHENYLETHYLENES AS WELL AS THEIR USE FOR THE PRODUCTION OF PHARMACEUTICAL AGENTS

[75] Inventors: Rolf Bohlmann; Joseph Heindl; Hermann Künzer; Yukishige Nishino; Karsten Parczyk; Martin Schneider, all of Berlin, Germany

[73] Assignee: Schering Aktiengesellschaft, Germany

[21] Appl. No.: 675,906

[22] Filed: Jul. 5, 1996

[30] Foreign Application Priority Data

Jul. 7, 1995 [DE] Germany .................. 195 26 146.1

[51] Int. Cl.$^6$ .................. A61K 31/10; C07C 317/12; C07C 321/18; C07C 321/20
[52] U.S. Cl. .................. 514/708; 514/709; 514/713; 568/27; 568/28; 568/33; 568/39
[58] Field of Search .................. 568/27, 28, 33, 568/39; 514/708, 709, 713

[56] References Cited

U.S. PATENT DOCUMENTS

| 4,536,516 | 8/1985 | Harper et al. | 514/514 |
| 5,378,705 | 1/1995 | Klaus et al. | 544/227.5 |

FOREIGN PATENT DOCUMENTS

| 2109426 | 10/1992 | Canada . |
| 93/13123 | 7/1993 | WIPO . |

OTHER PUBLICATIONS

Katzenellenbogen et al., "Efficient and Highly Selective Covalent Labeling of teh Estrogen Receptor with [$^3$H] Tamoxifen Aziridine," J. Biol. Chem., 258(6):3487–3495 (Mar. 25, 1983).

Robertson et al., "Antiestrogen Basicity–Activity Relationships: A Comparison of the Estrogen Receptor Binding and Antiuterotrophic Potencies of Several Analogues of (Z)–1, 2–Diphenyl–1–[4–[2–(dimethylamino)ethoxy]phenyl]–1–butene (Tamoxifen, Nolvadex) Having Altered Basicity," J. Med. Chem., 25(2):167–171 (Feb. 1982).

*Primary Examiner*—Alan L. Rotman
*Attorney, Agent, or Firm*—Millen, White, Zelano & Branigan, P.C.

[57] ABSTRACT

This invention describes the new triphenylethylenes of general formula I

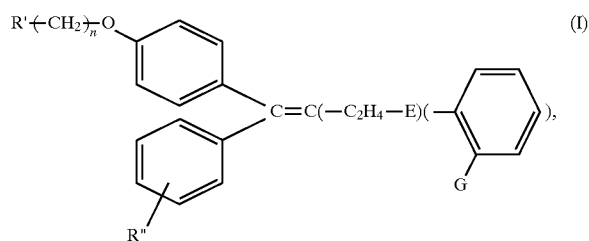

in which n means an integer from 1 to 10, R' means a sulfur-containing organic radical, R" means a hydrogen atom, an iodine atom or a hydroxy groups, E means a hydrogen atom, G means a hydrogen atom or E and G together mean a methylene bridge.

The new compounds have strong antiestrogenic properties and are suitable for the production of pharmaceutical agents, for example for treating breast cancer.

14 Claims, No Drawings

TRIPHENYLETHYLENES, PROCESS FOR THEIR PRODUCTION, PHARMACEUTICAL PREPARATIONS THAT CONTAIN THESE TRIPHENYLETHYLENES AS WELL AS THEIR USE FOR THE PRODUCTION OF PHARMACEUTICAL AGENTS

This invention relates to triphenylethylenes of general formula I

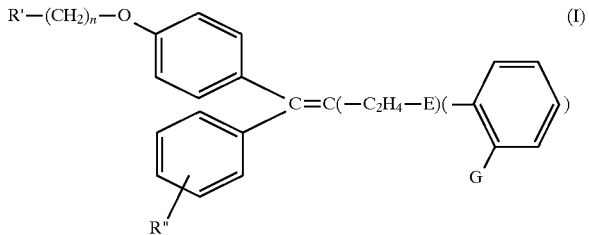

in which n means an integer from 1 to 10,

R' means a sulfur-containing organic radical,

R" means a hydrogen atom, an iodine atom or a hydroxy group,

E means a hydrogen atom,

G means a hydrogen atom or

E and G together mean a methylene bridge.

Sulfur-containing organic radical R' is preferably a group of formula

in which A means either a direct bond or an amino bridge —$NR^1$—$(CH_2)_1$—, in which $R^1$ stands for a hydrogen atom or a straight-chain or branched alkyl group with up to 6 carbon atoms and 1 stands for an integer from 1–5, x means 0, 1 or 2, B means either a direct bond or a saturated or unsaturated, aliphatic, linear or branched chain with up to 6 carbon atoms and R means a radical selected from among the group of substituents: a hydrogen atom, partially or completely fluorinated saturated, aliphatic, linear or branched alkyl group with 1 to 3 carbon atoms; phenyl, 1- or 2-naphthyl or heteroaryl radical; amide radical of formula —$C(O)NR^1R^2$, in which $R^1$ and $R^2$, identical or different, represent a hydrogen atom, a linear or branched alkyl radical with 1–8, preferably 1–6, carbon atoms, optionally substituted by one or more radicals, selected from among the aryl (e.g., those mentioned herein), alkyl- or dialkylamino, hydroxy, halogen or esterified (e.g., by $C_{1-8}$ alkyl) carboxyl radicals, or $R^1$ and $R^2$ with the nitrogen atom, to which they are bound, form a saturated or unsaturated heterocycle with 5 or 6 chain links (atoms), which optionally contains one or more additional heteroatoms, selected from among the nitrogen, oxygen and sulfur atoms, and optionally is substituted by an alkyl radical with 1 to 4 carbon atoms, whereby at least one of substituents $R^1$ and $R^2$ is not a hydrogen atom.

The R' and the alkylene group —$(CH_2)_n$ separating the phenoxy radical is preferably a di- to hexamethylene group, i.e., n is preferably 2, 3, 4, 5 or 6.

In a like manner, A can mean a direct bond or an amino bridge —$NR^1$—$(CH_2)_1$. In the latter case, a hydrogen atom or a methyl, ethyl, n-propyl or isopropyl, n-butyl, isobutyl or tertbutyl or a pentyl group is preferred for $R^1$. $R^1$ then especially means a methyl group.

Index 1 of the alkylene group is preferably 1, 2 or 3.

No preference is given to x in group —$S(O)_x$, so that the latter constitutes a sulfide; sulfoxide or sulfone.

Group B means a saturated or unsaturated, aliphatic, linear or branched chain with up to 6 carbon atoms. In this case, B preferably stands for a methylene to hexamethylene group or for the ethinediyl group.

Terminal substituent R is preferably a hydrogen atom, a perfluoromethyl or perfluoroethyl group, a phenyl radical, a 2-, 3- or 4-pyridinyl, a 2- or 3-furyl, a 2- or 3-thienyl, a 2- or 3-pyrrolyl, a 2-, 4- or 5-imidazolyl, a pyrazinyl, a 2-, 4- or 5-pyrimidinyl or a 3- or 4-pyridazinyl radical, an amide radical of formula —$C(O)NR^1R^2$, in which $R^1$ and $R^2$, independently of one another, mean a hydrogen atom, a methyl, ethyl, n-propyl or isopropyl, n-butyl, isobutyl or tert-butyl or a pentyl group and especially the combination of methyl-/isopropyl- or methyl-/tertbutyl-. If $R^1$ and $R^2$ with the nitrogen atom, to which they are bound, form a saturated or unsaturated heterocycle with 5 or 6 chain links, which optionally contains one or more additional heteroatoms, selected from among the nitrogen, oxygen and sulfur atoms, in this case this is especially the pyrrolidine, piperidine, morpholine or piperazine ring.

All above-mentioned radicals (H, OH, I) are equally considered for substituents R".

Substituents E and G stand either respectively for a hydrogen atom or together for a methylene bridge, so that the compounds of general formula I comprise the following two partial formulas:

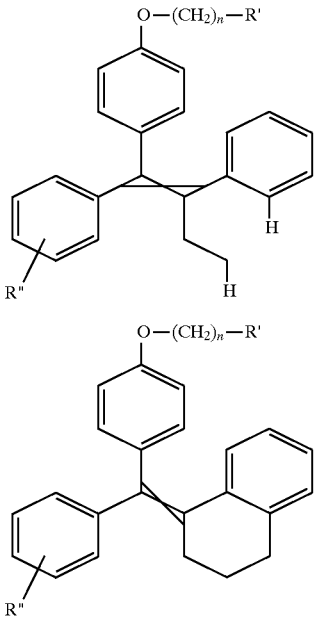

Crossed lines ⨯ between the two olefinic carbon atoms indicate that this double bond can be both E- and Z-configured. The absolute configuration cannot be determined from the start, since here in each case the priorities of the phenyl rings on the basis of their substitution must be observed.

When the compounds of general formula I are present or accumulate as E/Z mixtures, these mixtures can be separated, for example, by chromatography.

The meanings of n, A, x, B and R are selected together, so that —O—$(CH_2)_n$—R'[—O—$(CH_2)_n$—A—$S(O)_x$—B—R] preferably forms one of the following side chains:

—O—(CH$_2$)$_5$—SO—(CH$_2$)$_3$—C$_2$F$_5$
—O—(CH$_2$)$_5$—S—CH$_2$)$_3$—C$_2$F$_5$
—O—(CH$_2$)$_5$—SO$_2$—(CH$_2$)$_3$—C$_2$F$_5$
—O—CH$_2$)$_5$—SO$_2$—CH$_2$—(2-Pyridinyl)
—O—CH$_2$)$_5$—SO—CH$_2$—(2-Pyridinyl)
—O—CH$_2$)$_5$—S—CH$_2$—(2-Pyridinyl)
—O—(CH$_2$)$_6$—SO—CH$_2$)$_3$—C$_2$F$_5$
—O—(CH$_2$)$_5$—SO—CH$_2$—C≡C-Phenyl
—O—(CH$_2$)$_4$—SO—(CH$_2$)$_3$—C$_2$F$_5$
—O—(CH$_2$)$_2$—N(CH$_3$)—(CH$_2$)$_2$—SO$_2$—(CH$_2$)$_3$—C$_2$F$_5$
—O—(CH$_2$)$_2$—N(CH$_3$)—(CH$_2$)$_2$—SO—(CH$_2$)$_3$—C$_2$F$_5$
—O—(CH$_2$)$_6$—S—CH$_2$—C(O)—N(CH$_3$)(n-Butyl)
—O—(CH$_2$)$_6$—SO—CH$_2$—C(O)—N(CH$_3$)(n-Butyl)
—O—(CH$_2$)$_6$—SO$_2$—CH$_2$—C(O)—N(CH$_3$)(n-Butyl)
—O—(CH$_2$)$_2$—N(CH$_3$)—(CH$_2$)$_3$—SO—(CH$_2$)$_3$—C$_2$F$_5$
—O—(CH$_2$)$_2$—SO$_2$—(CH$_2$)$_3$—C$_2$F$_5$
—O—(CH$_2$)$_2$—N(CH$_3$)—(CH$_2$)$_3$—S—(CH$_2$)$_3$—C$_2$F$_5$
—O—CH$_2$)$_2$—SO—(CH$_2$)$_3$—C$_2$F$_5$
—O—CH$_2$)$_2$—S—(CH$_2$)$_3$—C$_2$F$_5$
—O—(CH$_2$)$_5$—SO—(CH$_2$)$_5$—CH$_3$
—O—(CH$_2$)$_5$—SO—(CH$_2$)$_3$—CH$_3$
—O—(CH$_2$)$_5$—SO—(CH$_2$)$_4$—CH$_3$
—O—(CH$_2$)$_3$—S—(CH$_2$)$_3$—C$_2$F$_5$
—O—(CH$_2$)$_3$—SO—(CH$_2$)$_3$—C$_2$F$_5$
—O—(CH$_2$)$_3$—N(CH$_3$)—(CH$_2$)$_2$—S—(CH$_2$)$_3$—C$_2$F$_5$
—O—(CH$_2$)$_3$—N(CH$_3$)—(CH$_2$)$_3$—S—(CH$_2$)$_3$—C$_2$F$_5$
—O—(CH$_2$)$_3$—N(CH$_3$)—(CH$_2$)$_2$—SO—(CH$_2$)$_3$—C$_2$F$_5$
—O—(CH$_2$)$_3$—N(CH$_3$)—(CH$_2$)$_3$—SO—(CH$_2$)$_3$—C$_2$F$_5$
—O—(CH$_2$)$_4$—S—CH$_2$—C(O)—N(CH$_3$) (n-Butyl)
—O—(CH$_2$)$_4$—SO—CH$_2$—C(O)—N(CH$_3$)(n-Butyl)
—O—(CH$_2$)$_5$—S—CH$_2$—C(O)-N(CH$_3$)(n-Butyl)
—O—(CH$_2$)$_5$—SO—CH$_2$—C(O)—N(CH$_3$)(n-Butyl)

The compounds mentioned below are preferred within the scope of this invention:

{5-[4-(1,2-Diphenyl-but-1-enyl)-phenoxy]-pentyl}-(4,4,5,5,5-pentafluoropentyl)-sulfide
{5-[4-(1,2-diphenyl-but-1-enyl)-phenoxy]-pentyl}-(4,4,5,5,5-pentafluoropentyl)-sulfoxide
{5-[4-(1,2-diphenyl-but-1-enyl)-phenoxy)-pentyl}-(4,4,5,5,5-pentafluoropentyl)-sulfone
4-(1-{4-[5-(4,4,5,5,5-pentafluoropentylsulfidyl)-pentyloxy]-phenyl}-2-phenyl-but-1-enyl)-phenol
4-(1-{4-[5-(4,4,5,5,5-pentafluoropentanesulfinyl)-pentyloxy]-phenyl}-2-phenyl-but-1-enyl)-phenol
4-((E,Z)-1-{4-[5-(4,4,5,5,5-pentafluoropentanesulfonyl)-pentyloxy]-phenyl}-2-phenyl-but-1-enyl)-phenol
(4,4,5,5,5-pentafluoropentyl)-{6-[4-((E,Z)-phenyl-1,2,3,4-tetrahydronaphth-1-ylidenemethyl)-phenoxy]-hexyl}-sulfoxide
(3-phenylprop-2-inyl)-{5-[4-((E,Z)-phenyl-1,2,3,4-tetrahydronaphth-1-ylidenemethyl)-phenoxy)-pentyl}-sulfoxide
{5-[4-((E,Z)-1,2-diphenyl-but-1-enyl)-phenoxy]-pentyl}-pyridin-2-ylmethyl-sulfoxide
{5-(4-(1,2-diphenyl-but-1-enyl)-phenoxy)-pentyl}-pyridin-2-ylmethyl-sulfide
4-((E,Z)-2-phenyl-1-{4-[5-(pyridin-2-ylmethylsulfidyl)-pentyloxy]-phenyl}-but-1-enyl)-phenol
4-((E,Z)-2-phenyl-1-{4-[5-(pyridin-2-ylmethanesulfinyl)-pentyloxy]-phenyl}-but-1-enyl)-phenol
4-((E,Z)-2-phenyl-1-{4-[5-(pyridin-2-ylmethanesulfonyl)-pentyloxy]-phenyl}-but-1-enyl)-phenol
(5-{4-[(E,Z)-1-(4-iodophenyl)-2-phenyl-but-1-enyl]-phenoxy}-pentyl)-(4,4,5,5,5-pentafluoropentyl)-sulfide
(5-{4-((E,Z)-1-(4-iodophenyl)-2-phenyl-but-1-enyl]-phenoxy}-pentyl)-(4,4,5,5,5-pentafluoropentyl)-sulfoxide
3-(1-{4-[5-(4,4,5,5,5-pentafluoropentylsulfidyl)-pentyloxy]-phenyl}-2-phenyl-but-1-enyl)-phenol
3-((E,Z)-1-{4-[5-(4,4,5,5,5-pentafluoropentanesulfinyl)-pentyloxy]-phenyl}-2-phenyl-but-1-enyl)-phenol
(E,Z)-1-{4-[5-(4,4,5,5,5-pentafluoropentylsulfinyl)-pentyloxy]phenyl}-1-(4-hydroxyphenyl)-2-phenyl-but-1-ene
(E)-1-{4-[5-(4,4,5,5,5-pentafluoropentylsulfinyl)-pentyloxy]-phenyl}-1-(4-hydroxyphenyl)-2-phenyl-but-1-ene
{5-[4-((E,Z)-1,2-diphenyl-but-1-enyl)-phenoxy)-pentyl}-pyridin-2-ylmethyl-sulfone
{5-[4-(1,2-diphenyl-but-1(Z)-enyl)-phenoxy]-pentyl}-(4,4,5,5,5-pentafluoropentyl)-sulfoxide
{5-[4-(1,2-diphenyl-but-1(E)-enyl)-phenoxy]-pentyl}-(4,4,5,5,5-pentafluoropentyl)-sulfoxide
4-(1-{4-[4-(4,4,5,5,5-pentafluoropentanesulfinyl)-butyloxy]-phenyl}-2-phenyl-but-1(E,Z)-enyl)-phenol
4-(1-{4-[6-(4,4,5,5,5-pentafluoropentanesulfinyl)-hexyloxy]-phenyl}-2-phenyl-but-1(E,Z)-enyl)-phenol
4-(1-{4-[(N-methyl-N-2-(4,4,5,5,5-pentafluoropentanesulfonyl)-ethyl-amino)-ethyloxy]-phenyl}-2-phenyl-but-1(E,Z)-enyl)-phenol
4-(1-{4-(2-(N-methyl-N-2-(4,4,5,5,5-pentafluoropentanesulfinyl)-ethyl-amino)-ethyloxy]-phenyl}-2-phenyl-but-1(E,Z)-enyl)-phenol
(Z)-4-{12-(4,4,5,5,5-pentafluoropentylsulfinyl)-1-[4-(5-(4,4,5,5,5-pentafluoropentylsulfinyl)-pentyloxy)-phenyl]-2-phenyldodec-1-enyl}-phenol
(E)-4-{12-(4,4,5,5,5-pentafluoropentylsulfinyl)-1-[4-(5-(4,4,5,5,5-pentafluoropentylsulfinyl)-pentyloxy)-phenyl]-2-phenyldodec-1-enyl)}-phenol
N-butyl-2-(6-{4-[1-(4-hydroxy-phenyl)-2-phenyl-but-1(E,Z)-enyl]-phenoxy}-hexylthio)-N-methylacetamide
N-butyl-2-(6-{4-[1-(4-hydroxy-phenyl)-2-phenyl-but-1(E,Z)-enyl]-phenoxy}-hexanesulfinyl)-N-methylacetamide
N-butyl-2-(6-{4-[1-(4-hydroxy-phenyl)-2-phenyl-but-1(E,Z)-enyl]-phenoxy}-hexanesulfonyl)-N-methylacetamide
(Z)-4-{12-(4,4,5,5,5-pentafluoropentylsulfonyl)-1-[4-(5-(4,4,5,5,5-pentafluoropentylsulfonyl)-pentyloxy)-phenyl]-2-phenyldodec-1-enyl}-phenol
4-(1-{4-[2-(4,4,5,5,5-pentafluoropentylthio)-ethyloxy]-phenyl}-2-phenyl-but-1(E,Z)-enyl)-phenol
4-(1-{4-[2-(4,4,5,5,5-pentafluoropentylsulfinyl)-ethyloxy]-phenyl}-2-phenyl-but-1(E,Z)-enyl)-phenol
4-(1-{4-[2-(N-methyl-N-3-(4,4,5,5,5-pentafluoropentylthio)-propyl-amino)-ethyloxy]-phenyl}-2-phenyl-but-1(E,Z)-enyl)-phenol
4-(1-{4-[2-(4,4,5,5,5-pentafluoropentylsulfonyl)-ethyloxy]-phenyl}-2-phenyl-but-1(E,Z)-enyl)-phenol
4-(1-{4-[2-(N-methyl-N-3-(4,4,5,5,5-pentafluoropentanesulfinyl)-propylamino-ethyloxy]-phenyl}-2-phenyl-but-1-(E,Z)-enyl)-phenol
4-(3-{3-[4-(4,4,5,5,5-pentafluoropentylthio)-propyloxy]phenyl}-2-phenyl-but-1(E,Z)-enyl)-phenol
4-(1-{4-[3-(N-methyl-N-2-(4,4,5,5,5-pentafluoropentylthio)-ethyl-amino)-propyloxy]-phenyl}-2-phenyl-but-1(E,Z)-enyl)-phenol
4-(1-{4-[3-(N-methyl-N-3-(4,4,5,5,5-pentafluoropentylthio)-propyl-amino)-propyloxy]-phenyl}-2-phenyl-but-1(E,Z)-enyl)-phenol 4-(1-{4-[3-(4,4,5,5,5-pentafluoropentylsulfinyl)-propyloxy]-phenyl}-2-phenyl-but-1(E,Z)-enyl)-phenol 4-(1-{4-[3-(N-methyl-N-2-(4,4,5,5,5-pentafluoropentanesulfinyl)-ethyl-amino)-propyloxy]-phenyl}-2-phenyl-but-1(E,Z)-enyl)-phenol 4-(1-{4-[3-(N-methyl-N-3-(4,4,5,5,5-pentafluoropentanesulfinyl)-propylamino-propyloxy]-phenyl}-2-phenyl-but-1(E,Z)-enyl)-phenol N-Butyl-2-(4-{4-[1-(4-hydroxy-phenyl)-2-phenyl-but-1(E,Z)-enyl-phenoxy}-butylsulfinyl)-N-methylacetamide N-Butyl-2-(4-{4-[1-(4-hydroxy-phenyl)-2-phenyl-but-1(E,Z)-enyl-phenoxy}-pentylsulfinyl)-N-methylacetamide;

It has now been found that the compounds of general formula I according to the invention have strong antiestrogenic properties (competitive antiestrogens).

Compounds with antiestrogenic properties, i.e., substances with inhibiting actions relative to estrogens, were already described in the literature.

As the compound that comes structurally closest to the existing compounds of general formula I, the antiestrogen tamoxifen can be cited (Eur. J. Cancer Clin. Oncol. 1985, 21, 985 and J. S. Patterson, "10 Years of Tamoxifen in Breast Cancer" in Hormonal Manipulation of Cancer; Peptides, Growth Factors and New (Anti)steroidal Agents, Raven Press, New York (1987)). Tamoxifen exhibits the same basic structure as the compounds according to the invention (R"=H, E and G, or H respectively); however, a 2-dimethylaminoethyl group is present on the phenoxy radical.

In the case of the compounds according to the invention, the activity is that of pure antiestrogens with even more antiestrogenic action than tamoxifen, or that of so-called partial antagonists, i.e., antiestrogens with estrogenic partial action such as tamoxifen itself. The agonistic, estrogenic action, however, is considerably less pronounced in each case in the compounds according to the invention than in tamoxifen. In contrast to tamoxifen, in the case of the partial antagonists of general formula I, their agonistic, estrogenic action occurs in a tissue-selective manner (tissues and bones), but not on other organs, which are known as target organs for estrogens (e.g., uterus, vagina, brain (CNS)).

In addition, steroidal antiestrogens are described in European Patent Application 0 138 504.

Newer steroidal antiestrogens that have an 11β-phenyl radical are described in EP-AS 0 384 842 and 0 629 635.

Antiestrogenic indole derivatives are already described in German Patent 32 32 968, in J. Med. Chem. 1983, 26, 113; J. Med. Chem., 1984, 27, 1439, Eur. J. Cancer. Clin. Oncol. 1985, 21, 531 and Cancer Treatment Reviews 1984, 11, 147 as well as N-aminoalkylindoles, which in addition to pronounced antiestrogenic action exhibit only low estrogenic activity, in European Patent Application 0 348 341.

Hydroxylated 2-phenylindoles, which are present in the form of diamine-platinum(II) complex compounds, are mentioned in German Laid-Open Specification 37 30 746.

A considerable number of different types of compounds—i.a., those of steroidal origin and those with 2-phenylindole skeletons—that act as antiestrogens and/or suppress estrogen biosynthesis, are disclosed in WO 93/10741.

The compounds of general formula I according to this application are distinguished by a new type of side chain on the phenoxy radical in comparison to the already known tamoxifen derivatives. This structural modification results in especially high antiestrogenically active compounds, as was demonstrated in transactivation tests. As mentioned an estrogenic partial action can also be present in the compounds according to the invention. The antiestrogenic and optionally estrogenic action of the compounds according to the invention was determined in a transactivation assay [Demirpence, E.; Duchesne, M.-J.; Badia, E.; Gagne, D.; and Pons, M.: MVLN Cells: A Bioluminescent MCF-7-Derived Cell Line to Study the Modulation of Estrogenic Activity; J. Steroid Molec. Biol.. Vol. 46, No. 3, 355–364 (1993) as well as Savouret, J. F.; Bailly, A.; Misrahi, M.; Rauch, C.; Redeuilh, G.; Chauchereau, A. and Milgrom, E.: Characterization of the Hormone Responsive Element Involved in the Regulation of the Progesterone Receptor Gene, The EMBO Journal Vol. 10, No. 7, 1875–1883 (1991)].

The antiproliferative activity of the new compounds in breast cancer cell lines is higher than that of tamoxifen.

The $IC_{50}$ values for the new compounds lie in the nanomolar range. In the HeLa cell line, the following $IC_{50}$ values are produced for the compounds of Examples 5, 12, 13 and 16 (test implementation according to the bibliographic references indicated above):

| Compound | $IC_{50}$ [nM] |
| --- | --- |
| 4-(1-{4-[5-(4,4,5,5,5-Pentafluoropentanesulfinyl)-pentyl-oxy]-phenyl}-2-phenyl-but-1-enyl)-phenol (Example 5) | 1.0 |
| 4-((E,Z)-2-phenyl-1-{4-[5-(pyrindin-2-ylmethylsulfidyl)-pentyloxy]-phenyl}-but-1-enyl)-phenol (Example 11) | 5.0 |
| 4-((E,Z)-2-phenyl-1-{4-[5-(pyridin-2-ylmethanesulfinyl)-pentyloxy]-phenyl}-but-1-enyl)-phenol (Example 12) | 2.8 |
| (5-{4-[(E,Z)-1-(4-iodophenyl)-2-phenyl-but-1-enyl]-phenoxy}-pentyl)-(4,4,5,5,5-pentafluoropentyl)-sulfoxide (Example 15) | 17.0 |

The compounds act in an inhibiting manner on the growth of hormone-dependent tumor cells, they especially inhibit the growth of estrogen-dependent human breast neoplasm cells (MCF-7).

The compounds according to the invention, especially if they are pure antiestrogens, thus are suitable for therapy of estrogen-dependent diseases, for example, breast cancer, endometrial carcinoma, prostatic hyperplasia, anovulatory infertility and melanoma.

The compounds of general formula I with tissue-selective estrogenic partial action can first be used for prophylaxis and therapy of osteoporosis and for the production of preparations for substitution therapy in premenopause, perimenopause and postmenopause (HRT) (Black, L. J.; Sato, M.; Rowlcy, E. R; Magee, D. E.; Bekele, A.; Williams, D. C.; Cullinan, G. J.; Bendele, R.; Kauffman, R. F.; Bensch, W. R.; Frolik, C. A.; Termine, J. D. and Bryant, H. U.: Raloxifene [LY 139481 HCl] Prevents Bone Loss and Reduces Serum Cholesterol Without Causing Uterine Hypertrophy in Ovariectomized Rats; J. Clin. Invest. 93: 63–69, 1994). The estrogenic partial action occurs exclusively on the desired target organ.

The invention also relates to pharmaceutical preparations that contain at least one compound of general formula I and the use of this compound for the production of pharmaceutical agents, especially for treating estrogen-dependent diseases and tumors and pharmaceutical agents for hormone substitution therapy (HRT).

The compounds according to the invention are suitable for the production of pharmaceutical compositions and preparations. The pharmaceutical compositions or pharmaceutical agents contain, as active ingredient, one or more of the compounds according to the invention, optionally in a mixture with other pharmacologically or pharmaceutically active substances. The production of the pharmaceutical agents is carried out in a known way, whereby the known and commonly used pharmaceutical adjuvants as well as other-commonly used vehicles and diluents can be used.

As such vehicles and adjuvants, for example, those are suitable that are recommended or indicated in the following bibliographic references as adjuvants for pharmaceutics, cosmetics and related fields: Ullmans Encyklopädie der technischen Chemie [Ullman's Encyclopedia of Technical Chemistry], Volume 4 (1953), pages 1 to 39; Journal of Pharmaceutical Sciences, Volume 52 (1963), page 918 and ff.; H. v. Czetsch-Lindenwald, Hilfsstoffe für Pharmazie und angrenzende Gebiete [Adjuvants for Pharmaceutics and Related Fields); Pharm. Ind. No. 2, 1961, page 72 and ff.; Dr. H. P. Fiedler, Lexikon der Hilfsstoffe für Pharmazie, Kosmetik und angrenzende Gebiete [Dictionary of Adjuvants for Pharmaceutics, Cosmetics and Related Fields] Cantor KG. Aulendorf in Würtemberg 1971.

The compounds can be administered orally or parenterally, for example, intraperitoneally, intramuscularly, subcutaneously or percutaneously. The compounds can also be implanted in the tissue. The amount of the compounds to be administered varies within a wide range and can cover any effective amount. Depending on the condition to be treated and the type of administration, the amount of administered compound can be 0.1–25 mg/kg of body weight, preferably 0.5–5 mg/kg of body weight, per day. In humans, this corresponds to a daily dose of 5 to 1250 mg.

For oral administration, capsules, pills, tablets, coated tablets, etc., are suitable. In addition to the active ingredient, the dosage units can contain a pharmaceutically compatible vehicle, such as, for example, starch, sugar, sorbitol, gelatin, lubricant, silicic acid, talc, etc. The individual dosage units for oral administration can contain, for example, 5 to 500 mg of active ingredient.

For parenteral administration, the active ingredients in a physiologically compatible diluent can be dissolved or suspended. As a diluent, very often oils with or without the addition of a solubilizer, a surfactant, a suspending agent or emulsifying agent are used. Examples of oils used are olive oil, peanut oil, cottonseed oil, soybean oil, castor oil and sesame oil.

The compounds can also be used in the form of a depot injection or an implant preparation, which can be formulated so that a delayed release of active ingredient is made possible.

As inert materials, implants can contain, for example, biodegradable polymers or synthetic silicones, such as, for example, silicone rubber. In addition, the active ingredients can be worked, for example, into a patch for percutaneous administration.

The production of the compounds according to the invention can be carried out according to various processes that are explained in more detail below. An overview on the methods for the production of triphenylethylenes (TPEs) is found in R. A. Magarian et al., "The Medicinal Chemistry of Nonsteroidal Antiestrogens: A Review"; Current Medicinal Chemistry, 1994, 1, pp. 61–104, see especially Chapter XI there. The definitions of the respective substituents can be found, if they do not occur in general formula I, in the reaction schemata below.

The compounds of general formula I are produced according to the invention, by a compound of general formula II being converted by Grignard reaction with a phenoxy compound of general formula III and dehydration to a compound of general formula IV. After cleavage of R''' in general formula IV, a compound of general formula VI is obtained, in which group X is replaced by radical R'. Compounds of general formula V, which optionally convert to compounds of general formula I after cleavage of protective groups and optionally oxidation, are obtained. The stereoisomeric forms that are formed with this method can be separated, for example, by chromatography.

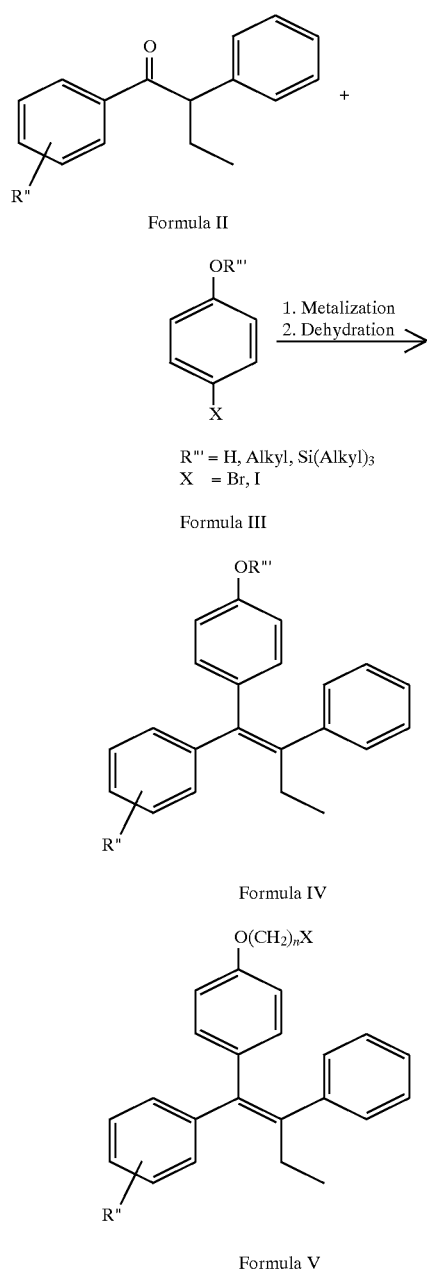

-continued

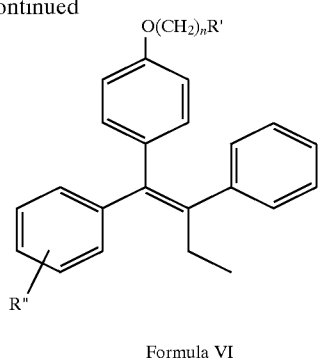

Formula VI

Another method according to the invention for the production of compounds of general formula I involves the reaction of two ketones of general formulas VII and VIII with "low valent" Ti salts according to McMurry to compounds of general formula IX and optionally subsequent cleavage of the protective groups and optionally oxidation to compounds of general formula I. The stereoisomeric forms formed can be separated by chromatography.

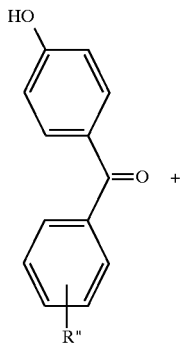

Formula VII

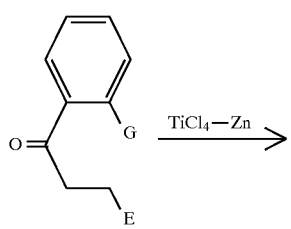

Formula VIII

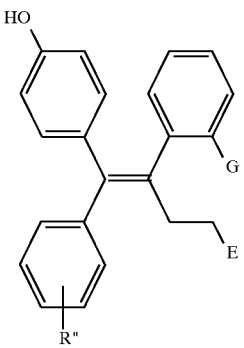

Formula IX

A third method [R. B. Miller*, M. I. Al-Hassan, J. Org. Chem. 50, 1985, 2121–2123] for the production of the compounds of general formula I according to the invention involves the reaction of 2-phenyl-1-trimethylsilylacetylene with diethylaluminum chloride in the presence of $Ti^{2+}$ complexes, bromation of the intermediate product with N-bromosuccinimide, palladium-catalyzed arylation and halogenation to compounds of general formula X. Renewed palladium-catalyzed arylation yields compounds of general formula IV, which can be converted to compounds of general formula I as described above. The compounds of general formula IV, which can be converted to compounds of general formula I as described above. The stereoisomeric forms can be produced specifically in this synthesis by the sequence of arylations.

1) $El_2AlCl$, $Cp_2TlCl_2$
2) N-Bromosuccinimide

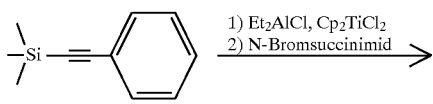

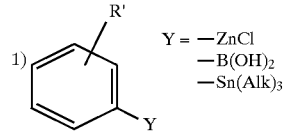

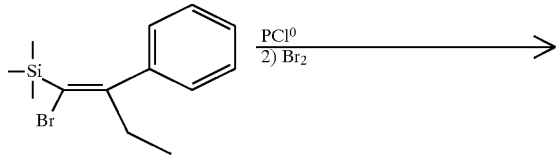

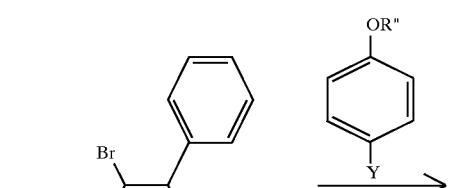

Formula X

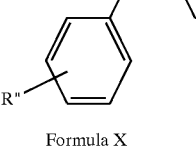

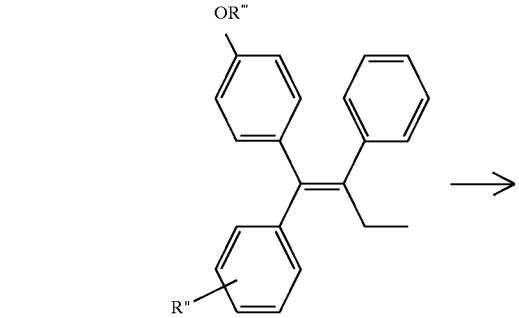

Formula IV

The examples below are used to explain this invention in more detail. Within the examples, the production of the required compounds of general formula II is also described. Compounds that are homologous to those reproduced in the examples below are obtained by a similar approach using corresponding homologous reagents.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German Application No. 19526146.1, filed Jul. 7, 1995, are hereby incorporated by reference.

EXAMPLE 1

{5-[4-(1,2-Diphenyl-but-1-enyl)-phenoxy]-pentyl}-(4,4,5,5,5-pentafluoropentyl)-sulfide a) 1-[4-(5-Bromopent-1-yloxy)-phenyl]-(E,Z)-1,2-diphenylbut-1-ene A solution of 18.4 g of 4-((E,Z)-1,2-diphenyl-but-1-enyl)-phenol [D. W. Robertson, J. A. Katzenellenbogen, D. J. Ellen, A. Rorke, B. S. Katzenellenbogen, J. Steroid Biochem., 1982, 16, 1–13] in 60 ml of dimethylformamide is stirred with 22 g of cesium carbonate and 15.5 g of 1,5-dibromopentane for 24 hours at room temperature. Then, it is diluted with ethyl acetate/diethyl ether, washed four times with water, once with saturated sodium chloride solution, dried on sodium sulfate and concentrated by evaporation in a vacuum, and chromatographed on silica gel with hexane/ethyl acetate. 19.5 g of 1-[4-(5-bromopent-1-yloxy)-phenyl]-(E,Z)-1,2-diphenyl-but-1-ene is obtained as oil.

b) {5-(4-((E,Z)-1,2-Diphenyl-but-1-enyl)-phenoxy)-pentyl}-(4,4,5,5,5-pentafluoropentyl)-sulfide A solution of 10.3 g of 4,4,4,5,5-pentafluoropentylthioacetate in 45 ml of methanol is mixed under argon at room temperature with 8.2 ml of 30% sodium methylate solution in methanol, and it is stirred for 0.25 more hour. This reaction mixture is added to a solution of 9.8 g of 1-[4-(5-bromopent-1-yloxy)-phenyl]-(E,Z)-1,2-diphenyl-but-1-ene in 25 ml of methanol and 10 ml of diethyl ether, and it is stirred for 18 hours at room temperature. Then, it is concentrated by evaporation in a vacuum, taken up with diethyl ether and water, the organic phases are washed neutral with water, washed with saturated sodium chloride solution, dried on sodium sulfate, concentrated by evaporation in a vacuum and chromatographed on silica gel with hexane/diethyl ether. 8.0 g of {5-[4-((E,Z)-1,2-diphenyl-but-1-enyl)-phenoxy]-pentyl}-(4,4,5,5,5-pentafluoropentyl)-sulfide is obtained as oil.

EXAMPLE 2

{5-[4-(1,2-Diphenyl-but-1-enyl)-phenoxy]-pentyl}-(4,4,5,5,5-pentafluoropentyl)-sulfoxide A solution of 3.5 g of {5-[4-((E,Z)-1,2-diphenyl-but-1-enyl)-phenoxy]-pentyl}-(4,4,5,5,5-pentafluoropentyl)-sulfide in 120 ml of methanol is mixed at room temperature with 6 ml of water and 1.58 mg of sodium periodate, and it is stirred for 18 hours. Then, it is evaporated to dryness in a vacuum, taken up with dichloromethane/water, washed with water, dried on sodium sulfate and concentrated by evaporation in a vacuum and chromatographed on silica gel with hexane/acetone. 3.5 g of {5-[4-(1,2-diphenyl-but-1-enyl)-phenoxy]-pentyl}-(4,4,5,5,5-pentafluoropentyl)-sulfoxide is obtained as colorless crystals with a melting point of 78°–82° C. Renewed chromatography yields pure {5-[4-((Z)-1,2-diphenyl-but-1-enyl)-phenoxy]-pentyl}-(4,4,5,5,5-pentafluoropentyl)-sulfoxide with a melting point of 84°–85° C. as well as pure {5-[4-((E)-1,2-diphenyl-but-1-enyl]-phenoxy]-pentyl}-(4,4,5,5,5-pentafluoropentyl)-sulfoxide with a melting point of 91°–93° C.

EXAMPLE 3

{5-[4-(1,2-Diphenyl-but-1-enyl)-phenoxy]-pentyl}-(4,4,5,5,5-pentafluoropentyl)-sulfone A solution of 3.5 g of {5-[4-((E,Z)-1,2-diphenyl-but-1-enyl)-phenoxy]-pentyl}-(4,4,5,5,5-pentafluoropentyl)-sulfide in 100 ml of tert-butanol is mixed at room temperature with 4.4 g of 55% 3-chloroperbenzoic acid, and it is stirred for 2 hours. Then, it is diluted with dichloromethane, washed with sodium hydrogen sulfite solution, 2N sodium hydroxide solution as well as water, dried on sodium sulfate and concentrated by evaporation in a vacuum and chromatographed on silica gel with hexane/acetone. 2.4 g of {5-[4-((E,Z)-1,2-diphenyl-but-1-enyl)-phenoxy]-pentyl}-(4,4,5,5,5-pentafluoropentyl)-sulfone is obtained as colorless crystals with a melting point of 77°–80° C.

EXAMPLE 4

4-(1-{4-[5-(4,4,5,5,5-Pentafluoropentylsulfidyl)-pentyloxy]-phenyl}-2-phenyl-but-1-enyl)-phenol a) 1-(4-Benzyloxy-phenyl)-1-(4-tert-butyldimethylsiloxyphenyl)-2-phenyl-butan-1-ol A solution of 19.32 g of (4-bromophenoxy)-tert-butyldimethylsilane in 50 ml of tetrahydrofuran is added in drops to a suspension of 1.58 g of magnesium chips in 100 ml of tetrahydrofuran at 80° C. bath temperature, and it is refluxed for 1 hour. Then, it is cooled to 0° C., and 6.0 g of 1-(4-benzyloxyphenyl)-2-phenyl-butan-1-one [D. W. Robertson; J. A. Katzenellenbogen; D. -J. Ellen; A. Rorke; B. S. Katzenellenbogen, J. Steroid Biochem., 1982, 16, 1–13] is added, and it is stirred for 24 more hours at room temperature. For working-up, 60 ml of saturated ammonium chloride solution is added, diluted with ethyl acetate, washed neutral with water, dried on sodium sulfate, concentrated by evaporation in a vacuum and chromatographed on silica gel with hexane/ethyl acetate. 9.1 g of 1-(4-benzyloxyphenyl)-1-(4-tert-butyldimethylsiloxy-phenyl)-2-phenyl-butan-1-ol is obtained as oil.

b) 4-[(E,Z)-1-(4-Benzyloxy-phenyl)-2-phenyl-but-1-enyl]-phenol

A solution of 8.8 g of 1-(4-benzyloxy-phenyl)-1-(4-tert-butyldimethylsiloxy-phenyl)-2-phenyl-butan-1-ol in 300 ml of methanol is mixed with 5 ml of concentrated hydrochloric acid and left at room temperature for 5 hours. Then, 100 ml of water and 300 ml of ethyl acetate are added, the organic phases are washed neutral with water, dried on sodium sulfate, concentrated by evaporation in a vacuum and recrystallized from hexane. 6.0 g of 4-[(E,Z)-1-(4-benzyloxy-phenyl)-2-phenyl-but-1-enyl]-phenol is obtained as colorless crystals with a melting point of 120°–125° C.

c) (E,Z)-1-(4-Benzyloxy-phenyl)-1-[4-(5-bromopent-1-yloxy)-phenyl]-2-phenylbut-1-ene A suspension of 5.7 g of 4-[(E,Z)-1-(4-benzyloxy-phenyl)-2-phenyl-but-1-enyl]-phenol in 50 ml of acetonitrile is stirred with 2.0 g of potassium carbonate and 3.8 ml of 1,5-dibromopentane for 5 hours at 60° C. After renewed addition of 0.5 g of potassium carbonate as well as 3 ml of 1,5-dibromopentane and another 15 hours at 60° C., it is mixed with water, acidified with 2N hydrochloric acid, diluted with ethyl acetate, washed twice with water, dried on sodium sulfate and concentrated by evaporation in a vacuum and chromatographed on silica gel with pentane/diethyl ether. 5.4 g of (E,Z)-1-(4-benzyloxy-phenyl)-1-[4-(5-bromopent-1-yloxy)-phenyl]-2-phenylbut-1-ene is obtained as oil.

d) (5-{4-[(E,Z)-1-(4-Benzyloxy-phenyl)-2-phenyl-but-1-enyl]-phenoxy}-pentyl)-(4,4,5,5,5-pentafluoropentyl)-sulfide A solution of 5 g of 4,4,4,5,5-pentafluoropentylthioacetate in 20 ml of methanol is mixed under argon at room temperature with 3.5 ml (18.7 mmol) of sodium methylate solution in methanol, and it is stirred for another 0.5 hour. This reaction mixture is added to a solution of 5.2 g of (E,Z)-1-(4-benzyloxy-phenyl)-1-[4-(5-bromopent-1-yloxy)-phenyl]-2-phenylbut-1-ene in 10 ml of methanol and 5 ml of diethyl ether, and it is stirred for 24 hours at room temperature. Then, it is concentrated by evaporation in a vacuum, taken up with diethyl ether and water, the organic phases are washed neutral with water, washed with saturated sodium chloride solution, dried on sodium sulfate, concentrated by evaporation in a vacuum and chromatographed on silica gel with pentane/diethyl ether. 6.1 g of (5-{4-[(E,Z)-1-(4-benzyloxy-phenyl)-2-phenyl-but-1-enyl]-phenoxy}-pentyl)-(4,4,5,5,5,-pentafluoropentyl)-sulfide is obtained.

e) 4-((E,Z)-1-{4-[5-(4,4,5,5,5-Pentafluoropentylsulfidyl)-pentyloxy]-phenyl}-2-phenyl-but-1-enyl)-phenol A solution of 6.1 g of (5-{4-[(E,Z)-1-(4-benzyloxy-phenyl)-2-phenyl-but-1-enyl]-phenoxy}-pentyl)-(4,4,5,5,5-pentafluoropentyl)-sulfide in 75 ml of dichloromethane is stirred at 0° C. with 2.95 g of N,N-dimethylaniline and 4.29 g of aluminum chloride for 2 hours in an ice bath. For working-up, it is mixed with 2N hydrochloric acid, diluted with dichloromethane, washed twice with water, dried on sodium sulfate and concentrated by evaporation in a vacuum and chromatographed on silica gel with pentane/diethyl ether. 3.4 g of 4-((E,Z)-1-{4-[5-(4,4,5,5,5-pentafluoropentylsulfidyl)-pentyloxy]-phenyl}-2-phenyl-but-1-enyl)-phenol is obtained as oil.

EXAMPLE 5

4-(1-{4-[5-(4,4,5,5,5-Pentafluoropentanesulfinyl)-pentyloxy]-phenyl}-2-phenyl-but-1-enyl)-phenol A solution of 1.7 g of 4-((E,Z)-1-{4-[5-(4,4,5,5,5-pentafluoropentylsulfidyl)-pentyloxy]-phenyl}-2-phenyl-but-1-enyl)-phenol in 60 ml of methanol is mixed at room temperature with 2.9 ml of water and 736 mg of sodium periodate, and it is stirred for 24 hours. Then, it is evaporated to dryness in a vacuum, taken up with dichloromethane/water, dried on sodium sulfate and concentrated by evaporation in a vacuum and chromatographed on silica gel with hexane/ethyl acetate. 1.5 g of 4-((E,Z)-1-{4-[5-(4,4,5,5,5-pentafluoropentanesulfinyl)-pentyloxy]-phenyl}-2-phenyl-but-1-enyl)-phenol is obtained as foam. Renewed chromatography yields pure 4-((Z)-1-{4-[5-(4,4,5,5,5-pentafluoropentanesulfinyl)-pentyloxy]-phenyl}-2-phenyl-but-1-enyl)-phenol with a melting point of 81°–82° C. as well as pure 4-((E)-1-{4-[5-(4,4,5,5,5-pentafluoropentanesulfinyl)-pentyloxy]-phenyl}-2-phenyl-but-1-enyl)-phenol with a melting point of 107°–108° C.

EXAMPLE 6

4-((E,Z)-1-{4-[5-(4,4,5,5,5-Pentafluoropentanesulfonyl)-pentyloxy]-phenyl}-2-phenyl-but-1-enyl)-phenol A solution of 1.5 g of 4-((E,Z)-1-{4-[5-(4,4,5,5,5-pentafluoropentylsulfidyl)-pentyloxy]-phenyl}-2-phenyl-but-1-enyl)-phenol in 40 ml of tert-butanol is mixed at room temperature with 1.75 g of 55% 3-chloroperbenzoic acid, and it is stirred for 2 hours. Then, it is diluted with dichloromethane, dried on sodium sulfate and concentrated by evaporation in a vacuum and chromatographed on silica gel with hexane/acetone. 1.1 g of 4-((E,Z)-1-{4-[5-(4,4,5,5,5-pentafluoropentanesulfonyl)-pentyloxy]-phenyl}-2-phenyl-but-1-enyl)-phenol, which melts after crystallization from diethyl ether/hexane at 125°–128° C., is obtained.

EXAMPLE 7

(4,4,5,5,5-Pentafluoropentyl)-{6-[4-((E,Z)-phenyl-1,2,3,4-tetrahydronaphth-1-ylidenemethyl)-phenoxy]-hexyl}-sulfoxide a) 6-{4-[(E,Z)-Phenyl-1,2,3,4-tetrahydronaphth-1-ylidenemethyl]-phenoxy}-1-hexanol A solution of 220 mg of 4-[(E,Z)-phenyl-1,2,3,4-tetrahydronaphth-1-ylidenemethyl)-phenol (Japan. Patent 05,112,510) and 140 mg of 6-bromo-1-hexanol in 5 ml of dimethylformamide is mixed with 252 mg of cesium carbonate, and the suspension is stirred for 20 hours at room temperature. The reaction mixture is mixed with water, shaken out three times with ethyl acetate, the organic phase is washed with saturated common salt solution, dried on sodium sulfate and concentrated by evaporation. The residue is chromatographed on silica gel with hexane/0–15% ethyl acetate. 189 mg of 6-{4-[(E,Z)-phenyl-1,2,3,4-tetrahydronaphth-1-ylidenemethyl]-phenoxy}-1-hexanol is obtained as yellow oil.

b) 6-{4-[(E,Z)-Phenyl-1,2,3,4-tetrahydronaphth-1-ylidenemethyl)-phenoxy}-hexyl-p-toluenesulfonate A solution of 1.65 mg of 6-{4-[(E,Z)-phenyl-1,2,3,4-tetrahydronaphth-1-ylidenemethyl]-phenoxy}-1-hexanol in 1.3 ml of pyridine is mixed at 0° C. with 300 mg of p-toluenesulfonic anhydride, and it is stirred for 5 hours at 0° C. The reaction mixture is poured into 2M hydrochloric acid, shaken out three times with ethyl acetate, the organic phase is washed with water, dried on sodium sulfate and concentrated by evaporation; The residue is chromatographed on silica gel with hexane/0–15% ethyl acetate. 160 mg of 6-{4-[(E,Z)-phenyl-1,2,3,4-tetrahydronaphth-1-ylidenemethyl]-phenoxy}-hexyl-p-toluenesulfonate is obtained as oil.

c) (4,4,5,5,5-Pentafluoropentyl)-{6-[4-((E,Z)-phenyl-1,2,3,4-tetrahydronaphth-1-ylidenemethyl)-phenoxy]-hexyl}-sulfide A solution of 122 mg of 4,4,5,5,5-pentafluoropentylthioacetate in 0.5 ml of methanol is mixed with 0.1 ml of a 30% sodium methanolate solution in methanol, and it is stirred for 30 minutes at room temperature. A solution of 150 mg of 6-{4-[(E,Z)-phenyl-1,2,3,4-tetrahydronaphth-1-ylidenemethyl]-phenoxy}-hexyl-p-toluenesulfonate in 0.5 ml of methanol and 2 ml of tetrahydrofuran is added to it, and the mixture is stirred for 20 hours at room temperature. The reaction mixture is concentrated by evaporation, mixed with water, shaken out with diethyl ether, the organic phase is washed with saturated common salt solution, dried on sodium sulfate and concentrated by evaporation. The residue is chromatographed on silica gel with hexane/0–10% ethyl acetate. 45 mg of (4,4,5,5,5-pentafluoropentyl)-{6-[4-((E,Z)-phenyl-1,2,3,4-tetrahydronaphth-1-ylidenemethyl)-phenoxy]-hexyl}-sulfide is obtained as yellow oil.

d) (4,4,5,5,5-Pentafluoropentyl)-{6-[4-((E,Z)-phenyl-1,2,3,4-tetrahydronaphth-1-ylidenemethyl)-phenoxy]-hexyl}-sulfoxide A solution of 38 mg of (4,4,5,5,5-pentafluoropentyl)-{6-[4-((E,Z)-phenyl-1,2,3,4-tetrahydronaphth-1-ylidenemethyl)-phenoxy]-hexyl}-sulfide in 1 ml of methanol, 1 ml of tetrahydrofuran and 0.8 ml of water is mixed with 15 mg of sodium periodate, and it is stirred for 20 hours at room temperature. The reaction mixture is mixed with water, shaken out with ethyl acetate, the organic phase is washed with saturated common salt solution, dried with sodium sulfate and concentrated by evaporation. The residue is chromatographed on silica gel with hexane/0–15% ethyl acetate. 40 mg of the title compound is obtained as yellow oil.

IR (Film): 2930, 2860, 1605, 1502, 1283, 1244, 1070, 833 $cm^{-1}$.

EXAMPLE 8

(3-Phenylprop-2-inyl)-{5-[4-((E,Z)-phenyl-1,2,3,4-tetrahydronaphth-1-ylidenemethyl)-phenoxy]-pentyl}-sulfoxide a) 1-[4-(5-Bromopentyloxy)-phenyl]-1-phenyl-1-(1,2,3,4-tetrahydronaphth-1-ylidene)-methane A solution of 500 mg of 4-[(E,Z)-phenyl-1,2,3,4-tetrahydronaphth-1-ylidenemethyl)-phenol (Japan. Patent 05,112,510) and 650 mg of 1,5-dibromopentane in 5 ml of acetonitrile is mixed with 345 mg of potassium carbonate, and it is stirred for 8 hours at 60° C. (bath temperature). The reaction mixture is mixed with water, shaken out with ethyl acetate, the organic phase is washed with saturated common salt solution, dried on sodium sulfate and concentrated by evaporation. The residue is chromatographed on silica gel with hexane/0–5% ethyl acetate. 625 mg of 1-[4-(5-bromopentyloxy)-phenyl]-1-phenyl-1-(1,2,3,4-tetrahydronaphth-1-ylidene)-methane is obtained as yellow oil.

b) 5-{4-[(E,Z)-Phenyl-1,2,3,4-tetrahydronaphth-1-ylidenemethyl]-phenoxy}-pentyl-thioacetate A solution of 625 mg of 1-[4-(5-bromopentyloxy)-phenyl]-1-phenyl-1-(1,2,3,4-tetrahydronaphth-1-ylidene)-methane in 10 ml of acetone is mixed with 309 mg of potassium thioacetate, and it is stirred for 4 hours at 80° C. (bath temperature). The reaction mixture is concentrated by evaporation, mixed with water, shaken out with diethyl ether, the organic phase is washed with saturated common salt solution, dried on sodium sulfate and concentrated by evaporation. The residue is chromatographed on silica gel with hexane/0–1% ethyl acetate. 490 mg of 5-{4-[(E,Z)-phenyl-1,2,3,4-tetrahydronaphth-1-ylidenemethyl]-phenoxy}-pentyl-thioacetate is obtained as oil.

c) (3-Phenylprop-2-inyl)-{5-[4-((E,Z)-phenyl-1,2,3,4-tetrahydronaphth-1-ylidenemethyl)-phenoxy]-pentyl}-sulfide A solution of 470 mg of 5-{4-[(E,Z)-phenyl-1,2,3,4-tetrahydronaphth-1-ylidenemethyl]-phenoxy}-pentyl-thioacetate in 1 ml of methanol and 1 ml of tetrahydrofuran is mixed with 0.2 ml of a 30% sodium methanolate solution in methanol, and it is stirred for 30 minutes at room temperature. A solution of 100 mg of 1-phenyl-3-bromo-1-propine* in 1 ml of tetrahydrofuran is added to it, and the mixture is stirred for 20 hours at room temperature. The reaction mixture is concentrated by evaporation, mixed with water, shaken out with diethyl ether, the organic phase is washed with saturated common salt solution, dried on sodium sulfate and concentrated by evaporation. The residue is chromatographed on silica gel with hexane/0–3% ethyl acetate. 337 mg of (3-phenylprop-2-inyl)-{5-[4-((E,Z)-phenyl-1,2,3,4-tetrahydronaphth-1-ylidenemethyl)-phenoxy]-pentyl}-sulfide is obtained as oil.

*1-Phenyl-3-bromo-1-propine is produced from 3-phenyl-2-propin-1-ol and phosphorus tribromide according to the method indicated by L. Brandsma in "Preparative Acetylenic Chemistry" Elsevier Verlag, 1988, p. 248.

d) (3-Phenylprop-2-inyl)-{5-[4-((E,Z)-phenyl-1,2,3,4-tetrahydronaphth-1-ylidenemethyl)-phenoxy]-pentyl}-sulfoxide Under the conditions of Example 7d, 150 mg of (3-phenylprop-2-inyl)-{5-[4-((E,Z)-phenyl-1,2,3,4-tetrahydronaphth-1-ylidenemethyl)-phenoxy]-pentyl}-sulfide is reacted with 140 mg of sodium periodate, worked up, and the crude product is chromatographed on silica gel with hexane/0–25% ethyl acetate. 91 mg of the title compound is obtained as yellow oil.

IR (Film): 3058, 2925, 2860, 1605, 1503, 1440, 1240, 1172, 1040, 835 cm$^{-1}$.

EXAMPLE 9

{5-[4-((E,Z)-1,2-Diphenyl-but-1-enyl)-phenoxy]-pentyl}-pyridin-2-ylmethyl-sulfoxide A solution of 5.1 g of {5-[4-((E,Z)-1,2-diphenyl-but-1-enyl)-phenoxy]-pentyl}-pyridin-2-ylmethyl-sulfide (Example 10) in 200 ml of methanol is mixed at room temperature with 10 ml of water and 2.61 g of sodium periodate, and it is stirred for 3 hours. Then, it is evaporated to dryness in a vacuum, taken up with dichloromethane/water, dried on sodium sulfate and concentrated by evaporation in a vacuum and chromatographed on silica gel with dichloromethane/acetone. 4.8 g of {5-[4-((E,Z)-1,2-diphenyl-but-1-enyl)-phenoxy]-pentyl}-pyridin-2-ylmethyl-sulfoxide is obtained as colorless crystals with a melting point of 107°–112° C.

EXAMPLE 10

{5-[4-(1,2-Diphenyl-but-1-enyl)-phenoxy]-pentyl}-pyridin-2-ylmethyl-sulfide a) {5-[4-((E,Z)-1,2-Diphenyl-but-1-enyl)-phenoxy]-pentyl}-thioacetate A solution of 9.7 g of (E,Z)-1-[4-(5-bromopent-1-yloxy)-phenyl]-1,2-diphenyl-but-1-ene in 160 ml of acetone is refluxed with 4.93 g of potassium thioacetate for 2 hours. Then, it is evaporated to dryness in a vacuum, mixed with water, extracted twice with diethyl ether, the organic phases are washed with saturated sodium chloride solution, dried on sodium sulfate and concentrated by evaporation in a vacuum and chromatographed on silica gel with pentane/diethyl ether. 7.5 g of {5-[4-((E,Z)-1,2-diphenyl-but-1-enyl)-phenoxy]-pentyl}-thioacetate is obtained as oil.

b) {5-[4-((E,Z)-1,2-Diphenyl-but-1-enyl)-phenoxy]-pentyl}-pyridin-2-ylmethyl-sulfide A solution of 7.3 g of {5-[4-((E,Z)-1,2-diphenyl-but-1-enyl)-phenoxy]-pentyl}-thioacetate in 75 ml of methanol and 45 ml of diethyl ether is stirred with 3.6 ml of 30% sodium methylate solution for 5 minutes at room temperature. The reaction solution that consists of 4.035 g of 2-picolyl chloride hydrochloride in 40 ml of methanol and 5.5 ml of 30% sodium methylate solution, which also is stirred for 5 minutes at room temperature, is added to it, and it is stirred for 2 more hours at room temperature. Then, it is evaporated to dryness in a vacuum, mixed with water, extracted with dichloromethane, the organic phases are washed with water, dried on sodium sulfate and concentrated by evaporation in a vacuum and chromatographed on silica gel with hexane/acetone. 6.3 g of {5-[4-((E,Z)-1,2-diphenyl-but-1-enyl)-phenoxy]-pentyl}-pyridin-2-ylmethyl-sulfide is obtained as oil.

EXAMPLE 11

4-((E,Z)-2-Phenyl-1-{4-[5-(pyridin-2-ylmethylsulfidyl)-pentyloxy]-phenyl}-but-1-enyl)-phenol a) S-{5-[4-((E,Z)-1,2-Diphenyl-but-1-enyl)-phenoxy]-pentyl}-thioacetate A solution of 7.3 g of (E,Z)-1-(4-benzyloxy-phenyl)-1-[4-(5-bromopent-1-yloxy)-phenyl]-2-phenylbut-1-ene in 100 ml of acetone is stirred with 2.99 g of potassium thioacetate for 1.5 hours at 80° C. bath temperature. For working-up, it is mixed with water, extracted with 300 ml of diethyl ether, the organic phases are washed with saturated sodium chloride solution, dried on sodium sulfate and concentrated by evaporation in a vacuum and chromatographed on silica gel with hexane/acetone. 6.4 g of S-{5-[4-((E,Z)-1,2-diphenyl-but-1-enyl)-phenoxy]-pentyl}-thioacetate is obtained as oil.

b) (5-{4-[(E,Z)-1-(4-Benzyloxy-phenyl)-2-phenyl-but-1-enyl]-phenoxy}-pentyl)-pyridin-2-ylmethyl-sulfide A solution of 6.2 g of S-{5-[4-((E,Z)-1,2-diphenyl-but-1-enyl)-phenoxy]-pentyl}-thioacetate in 50 ml of methanol and 30 ml of diethyl ether is stirred with 2.5 ml of 30% sodium methylate solution for 5 minutes at room temperature. The reaction solution that consists of 2.78 g of 2-picolyl chloride hydrochloride in 30 ml of methanol and 3.8 ml of 30% sodium methylate solution, which also is stirred for 5 minutes at room temperature, is added to it, and it is stirred for 2 more hours at room temperature. Then, it is evaporated to dryness in a vacuum, mixed with water, extracted with dichloromethane, the organic phases are washed with water, dried on sodium sulfate and concentrated by evaporation in a vacuum and chromatographed on silica gel with hexane/acetone. 6.7 g of (5-{4-[(E,Z)-1-(4-benzyloxy-phenyl)-2-phenyl-but-1-enyl]-phenoxy}-pentyl)-pyridin-2-ylmethyl-sulfide is obtained as oil.

c) 4-((E,Z)-2-Phenyl-1-{4-[5-(pyridin-2-ylmethylsulfidyl)-pentyloxy]-phenyl}-but-1-enyl)-phenol A solution of 6.6 g of (5-{4-[(E,Z)-1-(4-benzyloxy-phenyl)-2-phenyl-but-1-enyl]-phenoxy}-pentyl)-pyridin-2-ylmethyl-sulfide in 100 ml of dichloromethane is stirred at 0° C. with 4.13 g of N,N-dimethylaniline and 5.85 g of aluminum chloride for 2 hours in an ice bath. For working-up, it is mixed with sodium bicarbonate solution, basicity is established with 2N sodium hydroxide solution, filtered on Celite, rewashed with dichloromethane, the organic phases are washed with water, dried on sodium sulfate and concentrated by evaporation in a vacuum and chromatographed on silica gel with hexane/acetone. 3.5 g of 4-((E,Z)-2-phenyl-1-{4-[5-(pyridin-2-ylmethylsulfidyl)-pentyloxy]-phenyl}-but-1-enyl)-phenol is obtained as colorless crystals with a melting point of 115°–121° C.

EXAMPLE 12

4-((E,Z)-2-Phenyl-1-{4-[5-(pyridin-2-ylmethanesulfinyl)-pentyloxy]-phenyl}-but-1-enyl)-phenol A solution of 2 g of 4-((E,Z)-2-phenyl-1-{4-[5-(pyridin-2-ylmethylsulfidyl)-pentyloxy]-phenyl}-but-1-enyl)-phenol in 80 ml of methanol is mixed at room temperature with 4 ml of water and 995 mg of sodium periodate, and it is stirred for 18 hours. Then, it is evaporated to dryness in a vacuum, taken up with water/ethyl acetate, washed with water, dried on sodium sulfate and concentrated by evaporation in a vacuum and chromatographed on silica gel with dichloromethane/acetone. 1.8 g of 4-((E,Z)-2-phenyl-1-{4-[5-(pyridin-2-ylmethanesulfinyl)-pentyloxy]-phenyl}-but-1-enyl)-phenol is obtained as colorless crystals with a melting point of 116°–120° C.

EXAMPLE 13

4-((E,Z)-2-Phenyl-1-{4-[5-(pyridin-2-ylmethanesulfonyl)-pentyloxy]-phenyl}-but-1-enyl)-phenol A solution of 1 g of 4-((E,Z)-2-phenyl-1-{4-[5-(pyridin-2-ylmethylsulfonyl)-pentyloxy]-phenyl}-but-1-enyl)-phenol in 30 ml of 1,2-dichloroethane and 30 ml of tert-butanol is mixed at room temperature with 0.45 g of 55% 3-chloroperbenzoic acid, and it is stirred for 1 hour. Then, it is diluted with dichloromethane, washed with sodium sulfite solution and sodium bicarbonate solution, dried on sodium sulfate and concentrated by evaporation in a vacuum and chromatographed on silica gel with hexane/ethyl acetate. 0.9 g of 4-((E,Z)-2-phenyl-1-{4-[5-(pyridin-2-ylmethanesulfonyl)-pentyloxy]-phenyl}-but-1-enyl)-phenol is obtained as colorless crystals with a melting point of 112°–114° C.

EXAMPLE 14

(5-{4-[(E,Z)-1-(4-Iodophenyl)-2-phenyl-but-1-enyl]-phenoxy}-pentyl)-(4,4,5,5,5-pentafluoropentyl)-sulfide a) 1-(4-Benzyloxy-phenyl)-1-(4-iodophenyl)-2-phenyl-butan-1-ol A solution of 23.4 g of 1,4-diiodobenzene in 124 ml of tetrahydrofuran is mixed drop by drop at –70° C. under nitrogen with 45 ml of a 1.6 molar butyllithium solution, and it is stirred for 5 more minutes. Then, a solution of 18 g of 1-(4-benzyloxy-phenyl)-2-phenyl-butan-1-one [D. W. Robertson; J. A. Katzenellenbogen; D. J. Ellen; A. Rorke; B. S. Katzenellenbogen, J. Steroid Biochem., 1982, 16, 1–13] in 180 ml of tetrahydrofuran is added in drops, allowed to come to room temperature by completing the cooling, and it is stirred for 1 more hour. For working-up, 60 ml of saturated ammonium chloride solution is added, diluted with diethyl ether, washed neutral with water, dried on sodium sulfate, concentrated by evaporation in a vacuum and chromatographed on silica gel with pentane/diethyl ether. 31.5 g of 1-(4-benzyloxy-phenyl)-1-(4-iodophenyl)-2-phenyl-butan-1-ol is obtained as oil.

b) (E,Z)-1-(4-Benzyloxy-phenyl)-1-(4-iodophenyl)-2-phenyl-but-1-ene

A suspension of 31 g of 1-(4-benzyloxy-phenyl)-1-(4-iodophenyl)-2-phenyl-butan-1-ol in 550 ml of methanol and 150 ml of diethyl ether is mixed with 18 ml of concentrated hydrochloric acid, and it is stirred for 2 hours at room temperature. Then, the precipitated substance is filtered off, the mother liquor is concentrated by evaporation to 25%, and a second crystallizate is filtered off. 27.4 g of (E,Z)-1-(4-benzyloxy-phenyl)-1-(4-iodophenyl)-2-phenyl-but-1-ene is obtained as colorless crystals with a melting point of 125°–127° C.

c) 4-[(E,Z)-1-(4-Iodophenyl)-2-phenyl-but-1-enyl]-phenol

A solution of 26.6 g of (E,Z)-1-(4-benzyloxy-phenyl)-1-(4-iodophenyl)-2-phenyl-but-1-ene in 500 ml of dichloromethane is stirred at 0° C. with 19.6 ml of N,N-dimethylaniline and 27.4 g of aluminum chloride for 1 hour in an ice bath. For working-up, it is mixed in portions with 250 ml of 2N hydrochloric acid, diluted with dichloromethane, the organic phases are washed with water, dried on sodium sulfate and concentrated by evaporation in a vacuum and crystallized from hexane. 17.3 g of 4-[(E,Z)-1-(4-iodophenyl)-2-phenyl-but-1-enyl]-phenol is obtained as colorless crystals with a melting point of 133°–135° C.

d) (E,Z)-1-[4-(5-Bromopentyloxy)-phenyl]-1-(4-iodophenyl)-2-phenyl-but-1-ene

A suspension of 8 g of 4-[(E,Z)-1-(4-iodophenyl)-2-phenyl-but-1-enyl]-phenol in 100 ml of acetonitrile is stirred with 3.28 g of potassium carbonate and 2.9 ml of 1-bromo-5-chloropentane for 9.5 hours at 100° C. bath temperature. Then, it is mixed with water, extracted three times with ethyl acetate, washed twice with water, dried on sodium sulfate, concentrated by evaporation in a vacuum and chromatographed on silica gel with hexane/ethyl acetate. 9.2 g of (E,Z)-1-[4-(5-chloropentyloxy)-phenyl]-1-(4-iodophenyl)-2-phenyl-but-1-ene is obtained as oil.

A solution of 9.0 g of (E,Z)-1-[4-(5-chloropentyloxy)-phenyl)-1-(4-iodophenyl)-2-phenyl-but-1-ene in 275 ml of ethylmethylketone is stirred with 9 g of sodium iodide for 9.5 hours at 80° C. bath temperature. Then, it is concentrated by evaporation in a vacuum, added to water, extracted with ethyl acetate, washed neutral, dried on sodium sulfate, concentrated by evaporation in a vacuum, and chromatographed on silica gel with hexane/ethyl acetate. 10.3 g of (E,Z)-1-[4-(5-bromopentyloxy)-phenyl]-1-(4-iodophenyl)-2-phenyl-but-1-ene is obtained. By crystallization from hexane, pure (E)-1-[4-(5-bromopentyloxy)-phenyl]-1-(4-iodophenyl)-2-phenyl-but-1-ene is obtained as colorless crystals with a melting point of 78°–80° C.

e) (5-{4-[(E,Z)-1-(4-Iodophenyl)-2-phenyl-but-1-enyl]-phenoxy}-pentyl)-(4,4,5,5,5-pentafluoropentyl)-sulfide A solution of 5.17 g of 4,4,4,5,5-pentafluoropentylthioacetate in 22 ml of methanol is mixed under nitrogen at room temperature with 4.1 ml (22.2 mmol) of sodium methylate solution in methanol, and it is stirred for another 0.5 hour. This reaction mixture is added to a solution of 9.1 g of (E,Z)-1-[4-(5-iodopentyloxy)-phenyl]-1-(4-iodophenyl)-2-phenyl-but-1-ene in 80 ml of methanol and 30 ml of diethyl ether, and it is stirred for 2 hours at room temperature. Then, it is concentrated by evaporation in a vacuum, taken up with water, extracted with ethyl acetate, the organic phases are washed neutral with water, washed with saturated sodium chloride solution, dried on sodium sulfate, concentrated by evaporation in a vacuum and chromatographed on silica gel with hexane/ethyl acetate. 9.4 g of 5-{4-[(E,Z)-1-(4-iodophenyl)-2-phenyl-but-1-enyl]-phenoxy}-pentyl)-(4,4,5,5,5-pentafluoropentyl)-sulfide is obtained as oil.

EXAMPLE 15
(5-{4-[(E,Z)-1-(4-Iodophenyl)-2-phenyl-but-1-enyl]-phenoxy}-pentyl)-(4,4,5,5,5-pentafluoropentyl)-sulfoxide A solution of 8.0 g of 5-{4-[(E,Z)-1-(4-iodophenyl)-2-phenyl-but-1-enyl]-phenoxy}-pentyl)-(4,4,5,5,5-pentafluoropentyl)-sulfide in 260 ml of methanol is mixed at room temperature with 11 ml of water and 3.0 mg of sodium periodate, and it is stirred for 21 hours. Then, it is evaporated to dryness in a vacuum, taken up with water, extracted three times with ethyl acetate, dried on sodium sulfate and concentrated by evaporation in a vacuum and chromatographed on silica gel with dichloromethane/methyl-tert-butyl ether. 6.7 g of (5-{4-[(E,Z)-1-(4-iodophenyl)-2-phenyl-but-1-enyl]-phenoxy}-pentyl)-(4,4,5,5,5-pentafluoropentyl)-sulfoxide is obtained. Renewed chromatography on silica gel with hexane/ethyl acetate and crystallization from hexane yields 4.9 g of pure (5-{4-[(E)-1-(4-iodophenyl)-2-phenyl-but-1-enyl]-phenoxy}-pentyl)-(4,4,5,5,5-pentafluoropentyl)-sulfoxide as colorless crystals with a melting point of 85°–87° C.

EXAMPLE 16
3-(1-{4-[5-(4,4,5,5,5-Pentafluoro-pentylsulfidyl)-pentyloxy]-phenyl}-2-phenyl-but-1-enyl)-phenol a) 1-[4-(5-Chloropentyloxy)phenyl]-2-phenyl-butan-1-one A solution of 2.31 g (9.6 mmol) of 4-hydroxy-2'-phenylbutyrophenone and 1.56 ml (12.0 mmol) of 1-bromo-5-chloropentane in 200 ml of acetonitrile is mixed with 1.59 g (11.5 mmol) of potassium carbonate, and it is refluxed overnight (16 hours). For working-up,-the reaction mixture is taken up in ethyl acetate/water, the organic phase is washed with water and dried on sodium sulfate. After the drying agent is filtered off and after concentration by evaporation, the crude product is chromatographed on silica gel (hexane/ethyl acetate, gradient to 95:5), yield 2.79 g (84%) as oil.

b) 1-[4-(5-Iodopentyloxy)phenyl]-2-phenylbutan-1-one 2.79 g (8.09 mmol) of the chloride, described under 16a), in 50 ml of acetone is dissolved, mixed with 3.02 g (20.2 mmol) of sodium iodide and heated for three days while being stirred and refluxed. For working-up, precipitate is filtered out, it is concentrated by evaporation, and the residue is taken up in ethyl acetate. The organic phase is washed with water and dried on sodium sulfate. After drying agent is filtered out, the solvent is removed in a vacuum, and the iodide (3.43 g, 97%) is obtained as oil.

c) 1-[4-[5-(4,4,5,5,5-Pentafluoropentanesulfenyl) pentyloxy]-phenyl]-2-phenylbutan-1-one 0.77 g (14.2 mmol) of sodium methylate is added to a solution of 3.86 g (16.3 mmol) of 4,4,5,5,5-pentafluoropentylthioacetate in 30 ml of methanol, and it is stirred for 30 minutes with exclusion of oxygen at room temperature. Then, it is mixed with 3.13 g (7.17 mmol) of 1-[4-(5-iodopentyloxy)phenyl]-2-phenylbutan-1-one in 20 ml of tetrahydrofuran, and stirring is allowed to continue for two hours at room temperature. For working-up, the reaction mixture is added to water, extracted with ethyl acetate, the organic phase is washed with water and dried on sodium sulfate. The crude product is chromatographed on silica gel (cyclohexane/acetone 9:1), yield 3.53 g (97%) as oil.

d) 3-((E,Z)-1-{4-[5-(4,4,5,5,5-{Pentafluoropentylsulfidyl)-pentyloxy]-phenyl}-2-phenyl-but-1-enyl)-phenol 15 ml (24.5 mmol) of butyllithium in hexane is added in drops to a solution of 2.14 g (12 mmol) of 3-bromophenol in 40 ml of dry tetrahydrofuran at –70° C. After the addition is completed, the reaction mixture is allowed to thaw to 0° C., then cooled again to –70° C. and mixed drop by drop with a solution of 1.50 g (3.0 mmol) of the diarylbutanone in 10 ml of tetrahydrofuran that is described above. After one hour, the reaction is terminated by the addition of water. It is taken up in ethyl acetate, the organic phase is washed with water and dried on sodium sulfate. The crude product is chromatographed on silica gel (hexane/ethyl acetate, gradient to 4:1), yield 0.965 g (54%). For dehydration, 0.71 g (1.19 mmol) of this tert-alcohol is dissolved in 20 ml of methylene chloride and mixed with 0.1 g of p-toluenesulfonic acid while being stirred. Within one hour, dehydration is carried out at room temperature. The solvent is drawn off, and the residue is chromatographed on silica gel (hexane/ethyl acetate, 9:1), yield 0.564 g (82%) as oil (isomer mixture E/Z=1:3) after drying in a vacuum. The isomers can be separated by chromatography on silica gel (cyclohexane/acetone 85:15).

EXAMPLE 17
3-((E,Z)-1-{4-[5-(4,4,5,5,5-Pentafluoropentanesulfinyl)-pentyloxy]-phenyl}-2-phenyl-but-1-enyl)-phenol 3 drops of water are added to a solution of 61 mg (0.11 mmol) of the sulfide from Example 16 above in 2 ml of methanol, and it is mixed with 50 mg of sodium periodate. Then, it is allowed to stir for five hours at room temperature. For working-up, the reaction mixture is taken up in ethyl acetate/water, the organic phase is washed with water and dried on sodium sulfate. The crude product is chromatographed on silica gel (ethyl acetate). 48.7 mg (77%) of sulfoxide is obtained as an E/Z mixture (1:3) in the form of an oil.

EXAMPLE 18
4-((E,Z)-1-{4-[2-(N-Methyl-N-2-(4,4,5,5,5-pentafluoropentanesulfinyl)-ethyl-amino)-ethyloxy]-phenyl}-2-phenyl-but-1-enyl)-phenol a) (E,Z)-1-(4-Benzyloxyphenyl)-1-[4-(2-chloroethyloxy)-phenyl]-2-phenylbut-1-ene A solution of 20 g of 4-[(E,Z)-1-(4-benzyloxy-phenyl)-2-phenyl-but-1-enyl]-phenol in 264 ml of acetonitrile is stirred with 8.6 g of potassium carbonate and 5 ml of 1-bromo-2-chloroethane for 28 hours at 80° C. bath temperature. Then, it is concentrated by evaporation in a vacuum, added to water, extracted three times with ethyl acetate, washed with common salt solution, concentrated by evaporation in a vacuum and chromatographed on silica gel with hexane/ethyl acetate. 16.1 g of (E,Z)-1-(4-benzyloxyphenyl)-1-[4-(2-chloroethyloxy)-phenyl]-2-phenylbut-1-ene with a melting point of 65°–67° C. is obtained.

b) 4-{(E,Z)-1-[4-(2-Chloroethyloxy)-phenyl]-2-phenylbut-1-enyl}-phenol

A solution of 16 g of (E,Z)-1-(4-benzyloxyphenyl)-1-[4-(2-chloroethyloxy)-phenyl]-2-phenylbut-1-ene in 325 ml of dichloromethane is stirred at 0° C. with 13 ml of N,N-dimethylaniline for 5 minutes, and then it is stirred with 18.1 g of aluminum trichloride for 1.5 more hours at 0° C. Then, it is acidified with 2N hydrochloric acid while being cooled with ice, added to water, extracted with dichloromethane, washed with water and common salt solution, concentrated by evaporation in a vacuum and chromatographed on silica gel with hexane/ethyl acetate. 11.6 g of 4-{(E,Z)-1-[4-(2-chloroethyloxy)-phenyl]-2-phenyl-but-1-enyl}-phenol with a melting point of 120°–125° C. is obtained.

c) 4-{(E,Z)-1-[4-(2-Iodoethyloxy)-phenyl]-2-phenylbut-1-enyl}-phenol

A solution of 11.5 g of 4-{(E,Z)-1-[4-(2-chloroethyloxy)-phenyl]-2-phenyl-but-1-enyl}-phenol in 480 ml of ethylmethylketone is stirred with 16.8 g of sodium iodide for 27 hours at 80° C. bath temperature. Then, it is concentrated by evaporation in a vacuum, diluted with ethyl acetate, washed with water and common salt solution, concentrated by evaporation in a vacuum and chromatographed on silica gel with hexane/ethyl acetate. 13.8 g of 4-{(E,Z)-1-[4-(2-iodoethyloxy)-phenyl]-2-phenyl-but-1-enyl}-phenol with a melting point of 128°–133° C. is obtained.

d) 4-((E,Z)-1-{4-[2-(Methylamino)-ethyloxy]-phenyl}-2-phenyl-but-1-enyl)-phenol

A solution of 1 g of 4-{(E,Z)-1-[4-(2-iodoethyloxy)-phenyl]-2-phenyl-but-1-enyl}-phenol in 12.5 ml of dimethylformamide is stirred with 2 ml of a 40%, aqueous methylamine solution for 0.5 hour at 80° C. bath temperature. Then, it is added to water, extracted three times with ethyl acetate, washed neutral with common salt solution, dried on sodium sulfate, concentrated by evaporation in a vacuum and chromatographed on silica gel with hexane/ethyl acetate. 683 mg of 4-((E,Z)-1-{4-[2-(methylamino)-ethyloxy]-phenyl}-2-phenyl-but-1-enyl)-phenol is obtained as crystals with a melting point of 85°–88° C.

e) 4-((E,Z)-1-{4-[2-(N-Methyl-N-2-(4,4,5,5,5-pentafluoropentylthio)-ethyl-amino)-ethyloxy]-phenyl}-2-phenyl-but-1-enyl)-phenol A solution of 800 mg of 4-((E,Z)-1-{4-[2-(methylamino)-ethyloxy]-phenyl}-2-phenyl-but-1-enyl)-phenol in 12 ml of dimethylformamide is mixed drop by drop with 1.2 g of (2-iodoethyl)-(4,4,5,5,5-pentafluoropentyl)-sulfide in 2 ml of dimethylformamide, and it is stirred for 3 hours at 80° C. bath temperature. Then, it is added to water, extracted three times with ethyl acetate, dried on sodium sulfate, concentrated by evaporation in a vacuum and chromatographed on silica gel with hexane/ethyl acetate. 512 mg of 4-((E,Z)-1-{4-[2-(N-methyl-N-2-(4,4,5,5,5-pentafluoropentylthio)-ethyl-amino)-ethyloxy]-phenyl}-2-phenyl-but-1-enyl)-phenol is obtained as oil.

f) 4-((E,Z)-1-{4-[2-(N-Methyl-N-2-(4,4,5,5,5-pentafluoropentanesulfinyl)-ethyl-amino)-ethyloxy]-phenyl}-2-phenyl-but-1-enyl)-phenol 0.5 ml of water is added to a solution of 300 mg of 4-((E,Z)-1-{4-[2-(N-methyl-N-2-(4,4,5,5,5-pentafluoropentylthio)-ethyl-amino)-ethyloxy]-phenyl}-2-phenyl-but-1-enyl)-phenol in 10 ml of methanol, and it is mixed with 175 mg of sodium periodate. Then, it is allowed to stir for 6.5 hours at room temperature. For working-up, the reaction mixture is taken up in ethyl acetate/water, the organic phase is washed with water and dried on sodium sulfate. The crude product is chromatographed on silica gel (dichloromethane/acetone). 177 mg of 4-((E,Z)-1-{4-[(2-(N-methyl-N-2-(4,4,5,5,5-pentafluoropentanesulfinyl)-ethylamino)-ethyloxy]-phenyl}-2-phenyl-but-1-enyl)-phenol is obtained as an E/Z mixture (1:1) with a melting point of 72°–78° C.

EXAMPLE 19

4-(1-{4-[(N-Methyl-N-2-(4,4,5,5,5-pentafluoropentanesulfonyl)-ethyl-amino)-ethyloxy]-phenyl}-2-phenyl-but-1(E,Z)-enyl)-phenol 310 mg of m-chloroperbenzoic acid is added in portions to a solution of 620 mg of 4-((E,Z)-1-{4-[2-(N-methyl-N-2-(4,4,5,5,5-pentafluoropentylthio)-ethyl-amino)-ethyloxy]-phenyl}-2-phenyl-but-1-enyl)-phenol in 20 ml of dichloromethane at 0° C. Then, it is allowed to stir for 2 hours at 0° C. For working-up, it is diluted with dichloromethane, the organic phase is washed with water and dried on sodium sulfate. The crude product is chromatographed on silica gel (hexane/ethyl acetate). 350 mg of 4-((E,Z)-1-{4-[2-(N-methyl-N-2-(4,4,5,5,5-pentafluoropentanesulfonyl)-ethyl-amino)-ethyloxy]-phenyl}-2-phenyl-but-1-enyl)-phenol is obtained as an E/Z mixture (1:1) with a melting point of 126°–129° C.

EXAMPLE 20

N-Butyl-2-(6-{4-[(E,Z)-1-(4-hydroxy-phenyl)-2-phenyl-but-1-enyl]-phenoxy}-hexylthio)-N-methylacetamide a) (E,Z)1-(4-Benzyloxyphenyl)-1-[4-(6-chlorohexyloxy)-phenyl]-2-phenylbut-1-ene A solution of 4 g of 4-[(E,Z)-1-(4-benzyloxy-phenyl)-2-phenyl-but-1-enyl]-phenol in 53 ml of acetonitrile is stirred with 1.73 g of potassium carbonate and 1.78 ml of 1-bromo-6-chlorohexane for 24 hours at 100° C. bath temperature. Then, it is concentrated by evaporation in a vacuum, added to water, extracted with ethyl acetate, washed with common salt solution, dried on sodium sulfate, concentrated by evaporation in a vacuum and chromatographed on silica gel with hexane/ethyl acetate. 4.85 g of (E,Z)1-(4-benzyloxyphenyl)-1-[4-(6-chlorohexyloxy)-phenyl]-2-phenylbut-1-ene with a melting point of 82°–85° C. is obtained.

b) (E,Z)1-(4-Benzyloxyphenyl)-1-[4-(6-iodohexyloxy)-phenyl]-2-phenylbut-1-ene

A solution of 1.85 g of (E,Z)1-(4-benzyloxyphenyl)-1-[4-(6-chlorohexyloxy)-phenyl]-2-phenylbut-1-ene in 65 ml of ethylmethylketone is stirred with 9 g of sodium iodide for 24 hours at 80° C. bath temperature. Then, it is concentrated by evaporation in a vacuum, added to water, extracted with ethyl acetate, washed neutral, dried on sodium sulfate, concentrated by evaporation in a vacuum, and chromatographed on silica gel with hexane/ethyl acetate. 2.2 g of (E,Z)1-(4-benzyloxyphenyl)-1-[4-(6-iodohexyloxy)-phenyl]-2-phenylbut-1-ene is obtained.

c) 6-{4-[(E,Z)-1-(4-Benzyloxy-phenyl)-2-phenyl-but-1-enyl]-phenoxy}-hexyl-thioacetate A solution of 2.2 g of (E,Z)1-(4-benzyloxyphenyl)-1-[4-(6-iodohexyloxy)-phenyl]-2-phenylbut-1-ene in 30 ml of acetone is stirred with 1.22 g of potassium thioacetate for 3 hours at 60° C. bath temperature. Then, it is concentrated by evaporation in a vacuum, added to water, extracted with ethyl acetate, washed neutral, dried on sodium sulfate, concentrated by evaporation in a vacuum and chromatographed on silica gel with hexane/ethyl acetate. 1.6 g of 6-{4-[(E,Z)-1-(4-benzyloxy-phenyl)-2-phenyl-but-1-enyl]-phenoxy}-hexyl-thioacetate with a melting point of 70°–72° C. is obtained.

d) 2-(6-{4-[(E,Z)-1-(4-Benzyloxy-phenyl)-2-phenyl-but-1-enyl]-phenoxy}-hexylthio)-N-butyl-N-methylacetamide A solution of 1.5 g of (E,Z)1-(4-benzyloxyphenyl)-1-[4-(6-iodohexyloxy)-phenyl]-2-phenylbut-1-ene in 10 ml of methanol and 5 ml of tetrahydrofuran is stirred at room temperature with 0.5 ml of a 30% sodium methylate solution for 0.5 hour, then it is mixed drop by drop with a solution of 625 mg of N-butyl-N-methyl-bromoacetamide in 1 ml of tetrahydrofuran and stirred for another 2 hours at room temperature. Then, it is added to water, extracted with ethyl acetate, washed with common salt solution, dried on sodium sulfate, concentrated by evaporation in a vacuum and chromatographed on silica gel with hexane/ethyl acetate. 1.4 g of 2-(6-{4-[(E,Z)-1-(4-benzyloxy-phenyl)-2-phenyl-but-1-enyl]-phenoxy}-hexylthio)-N-butyl-N-methylacetamide is obtained as oil.

e) N-Butyl-2-(6-{4-[(E,Z)-1-(4-hydroxy-phenyl)-2-phenyl-but-1-enyl]-phenoxy}-hexylthio)-N-methylacetamide A solution of 1.3 g of 2-(6-{4-[(E,Z)-1-(4-benzyloxyphenyl)-2-phenyl-but-1-enyl]-phenoxy}-hexylthio)-N-butyl-N-methylacetamide in 20 ml of dichloromethane is stirred at 0° C. with 0.76 ml of N,N-dimethylaniline for 5 minutes and then stirred with 1.06 g of aluminum trichloride for 3 more hours at 0° C. Then, it is acidified with 2N hydrochloric acid while being cooled with ice, added to water, extracted with dichloromethane, washed with water and common salt solution, concentrated by evaporation in a vacuum and chromatographed on silica gel with hexane/ethyl acetate. 1.04 g of N-butyl-2-(6-{4-[(E,Z)-1-(4-hydroxy-phenyl)-2-phenyl-but-1-enyl]-phenoxy}-hexylthio)-N-methylacetamide is obtained as oil.

EXAMPLE 21

N-Butyl-2-(6-{4-[(E,Z)-1-(4-hydroxy-phenyl)-2-phenyl-but-1-enyl]-phenoxy}-hexanesulfinyl)-N-methylacetamide 1 ml of water is added to a solution of 600 mg of N-butyl-2-(6-{4-[(E,Z)-1-(4-hydroxy-phenyl)-2-phenyl-but-1-enyl]-phenoxy}-hexylthio)-N-methylacetamide in 20 ml of methanol, and it is mixed with 252 mg of sodium periodate. Then, it is allowed to stir for 17 hours at room temperature. For working-up, the reaction mixture is taken up in ethyl acetate/water, the organic phase is washed with water and dried on sodium sulfate. The crude product is chromatographed on silica gel (dichloromethane/acetone). 501 mg of N-butyl-2-(6-{4-[(E,Z)-1-(4-hydroxy-phenyl)-2-phenyl-but-1-enyl]-phenoxy}-hexanesulfinyl)-N-methylacetamide with a melting point of 75°–79° C. is obtained.

EXAMPLE 22

N-Butyl-2-(6-{4-[(E,Z)-1-(4-hydroxy-phenyl)-2-phenyl-but-1-enyl]-phenoxy}-hexanesulfonyl)-N-methylacetamide A solution of 200 mg of N-butyl-2-(6-{4-[(E,Z)-1-(4-hydroxyphenyl)-2-phenyl-but-1-enyl]-phenoxy}-hexanesulfinyl)-N-methylacetamide in 10 ml of dichloromethane is mixed at 0° C. with 100 mg of m-chloroperbenzoic acid in portions, and it is stirred for 2 hours at room temperature. For working-up, it is mixed with sodium thiosulfate, added to water, extracted with dichloromethane, the organic phase is washed with water and dried on sodium sulfate. The crude product is chromatographed on silica gel (hexane/ethyl acetate). 128 mg of N-butyl-2-(6-{4-[(E,Z)-1-(4-hydroxy-phenyl)-2-phenyl-but-1-enyl]-phenoxy}-hexanesulfonyl)-N-methylacetamide with a melting point of 52°–55° C. is obtained.

In addition, the following compounds have been produced in an analogous manner:

4-(1-{4-[4-(4,4,5,5,5-Pentafluor-pentylsulfinyl)-butyloxy]-phenyl}-2-phenyl-but-1(E,Z)-enyl)-phenol; m.p. 103°–110° C.

4-(1-{4-[6-(4,4,5,5,5-Pentafluor-pentylsulfinyl)-hexyloxy]-phenyl}-2-phenyl-but-1(E,Z)-enyl)-phenol; m.p. 72°–76° C.

4-(1-{4-[2-(4,4,5,5,5-Pentafluor-pentylsulfinyl)-ethyloxy]-phenyl}-2-phenyl-but-1(E,Z)-enyl)-phenol; m.p. 76°–80° C.

4-(1-{4-[2-(4,4,5,5,5-Pentafluor-pentylsulfonyl)-ethyloxy]-phenyl}-2-phenyl-but-1(E,Z)-enyl)-phenol; m.p. 60°–63° C.

4-(1-{4-[2-(N-Methyl-N-3-(4,4,5,5,5-Pentafluor-pentylsulfinyl)propyl-amino-ethyloxy]-phenyl}-2-phenyl-but-1(E,Z)-enyl)-phenol; m.p. 46°–50° C.

4-(1-{4-[3-(4,4,5,5,5-Pentafluor-pentansulfinyl)-propyloxy]-phenyl}-2-phenyl-but-1(E,Z)-enyl)-phenol; m.p. 69°–73° C.

4-(1-{4-[3-(N-Methyl-N-2-(4,4,5,5,5-Pentafluor-pentylsulfinyl)ethyl-amino-propyloxy]-phenyl}-2-phenyl-but-1(E,Z)-enyl)-phenol; m.p. 63°–68° C.

4-(1-{4-[3-(N-Methyl-N-3-(4,4,5,5,5-Pentafluor-pentylsulfinyl)propyl-amino-propyloxy]-phenyl}-2-phenyl-but-1(E,Z)-enyl)-phenol; m.p. 52°–55° C.

N-Butyl-2-(4-{4-[1-(4-hydroxy-phenyl)-2-phenyl-but-1(E,Z)-enyl-phenoxy}-butylsulfinyl)-N-methylacetamid., m.p. 43°–47° C.

N-Butyl-2-(4-{4-[1-(4-hydroxy-phenyl)-2-phenyl-but-1(E,Z)-enyl-phenoxy}-pentylsulfinyl)-N-methylacetamid., m.p. 38°–41° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A triphenylethylene of the formula

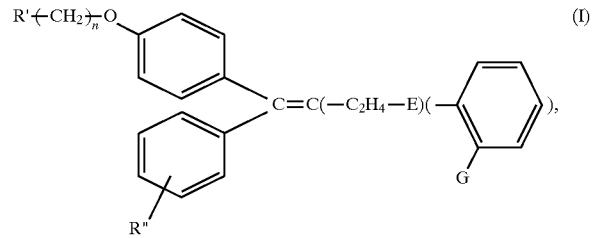

wherein n is an integer from 1 to 10,

R' is a group of formula

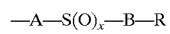

wherein

A is either a direct bond or an amino bridge —NR$^1$—(CH$_2$)$_1$—, wherein

R$^1$ is a hydrogen atom or a straight-chain or branched alkyl group with up to 6 carbon atoms and 1 stands for an integer from 1–5, x is 0, 1 or 2, B is either a direct bond or a saturated or unsaturated, aliphatic, linear or branched chain with up to 6 carbon atoms and R is a hydrogen atom; a partially or completely fluorinated, saturated, aliphatic, linear or branched C$_{1-3}$-alkyl group; phenyl, or 1- or 2-naphthyl; an amide radical of formula —C(O)NR$^1$R$^2$, wherein R$^1$ and R$^2$ are identical or different and are a hydrogen atom, a linear or branched C$_{1-8}$-alkyl radical, optionally substituted by one or more radicals selected from aryl, alkyl- and dialylamino, hydroxy, halogen or esterified carboxyl, R" is a hydrogen atom, an iodine atom or a hydroxy group, E is a hydrogen atom, G is a hydrogen atom or E and G together are a methylene bridge.

2. A triphenylethylene according to claim 1, in which n is 2, 3, 4, 5 or 6.

3. A triphenylethylene according to claim 1, in which R" is a hydrogen atom.

4. A triphenylethylene according to claim 1, in which R" is a hydroxy group.

5. A triphenylethylene according to claim 1, in which R" is an iodine atom.

6. A triphenylethylene according to claim 1, in which E and G each mean a hydrogen atom.

7. A triphenylethylene according to claim 1, in which E and G together mean a methylene bridge.

8. A triphenylethylene according to claim 1, comprising E-isomers when E and G are H or when E and G form a methylene bridge.

9. A triphenylethylene according to claim 1, comprising Z-isomers when E and G are H or when E and G form a methylene bridge.

10. A triphenylethylene according to claim 1, wherein —O—(CH$_2$)$_n$—R' is selected from the group of substituents —O—CH$_2$)$_5$—SO—(CH$_2$)$_3$—C$_2$F$_5$
—O—(CH$_2$)$_5$—S—CH$_2$)$_3$—C$_2$F$_5$
—O—(CH$_2$)$_5$—SO$_2$—(CH$_2$)$_3$—C$_2$F$_5$
—O—CH$_2$)$_5$—SO$_2$—CH$_2$—(2-Pyridinyl)
—O—CH$_2$)$_5$—SO—CH$_2$—(2-Pyridinyl)
—O—(CH$_2$)$_5$—S—CH$_2$—(2-Pyridinyl)
—O—(CH$_2$)$_6$—SO—CH$_2$)$_3$—C$_2$F$_5$
—O—(CH$_2$)$_5$—SO—CH$_2$—C≡C-Phenyl
—O—(CH$_2$)$_4$—SO—(CH$_2$)$_3$—C$_2$F$_5$
—O—(CH$_2$)$_2$—N(CH$_3$)—(CH$_2$)$_2$—SO$_2$—(CH$_2$)$_3$—C$_2$F$_5$
—O—(CH$_2$)$_2$—N(CH$_3$)—(CH$_2$)$_2$—SO—(CH$_2$)$_3$—C$_2$F$_5$
—O—(CH$_2$)$_6$—S—CH$_2$—C(O)—N(CH$_3$)(n-Butyl)
—O—(CH$_2$)$_6$—SO—CH$_2$—C(O)—N(CH$_3$)(n-Butyl)
—O—(CH$_2$)$_6$—SO$_2$—CH$_2$—C(O)—N(CH$_3$)(n-Butyl)
—O—(CH$_2$)$_2$—N(CH$_3$)—(CH$_2$)$_3$—SO—(CH$_2$)$_3$—C$_2$F$_5$
—O—(CH$_2$)$_2$—SO$_2$—(CH$_2$)$_3$—C$_2$F$_5$
—O—(CH$_2$)$_2$—N(CH$_3$)—(CH$_2$)$_3$—S—(CH$_2$)$_3$—C$_2$F$_5$
—O—CH$_2$)$_2$—SO—(CH$_2$)$_3$—C$_2$F$_5$
—O—CH$_2$)$_2$—S—(CH$_2$)$_3$—C$_2$F$_5$
—O—(CH$_2$)$_5$—SO—(CH$_2$)$_5$—CH$_3$
—O—(CH$_2$)$_5$—SO—(CH$_2$)$_3$—CH$_3$
—O—(CH$_2$)$_5$—SO—(CH$_2$)$_4$—CH$_3$
—O—(CH$_2$)$_3$—S—(CH$_2$)$_3$—C$_2$F$_5$
—O—(CH$_2$)$_3$—SO—(CH$_2$)$_3$—C$_2$F$_5$
—O—(CH$_2$)$_3$—N(CH$_3$)—(CH$_2$)$_2$—S—(CH$_2$)$_3$—C$_2$F$_5$
—O—(CH$_2$)$_3$—N(CH$_3$)—(CH$_2$)$_3$—S—(CH$_2$)$_3$—C$_2$F$_5$
—O—(CH$_2$)$_3$—N(CH$_3$)—(CH$_2$)$_2$—SO—(CH$_2$)$_3$—C$_2$F$_5$
—O—(CH$_2$)$_3$—N(CH$_3$)—(CH$_2$)$_3$—SO—(CH$_2$)$_3$—C$_2$F$_5$
—O—(CH$_2$)$_4$—S—CH$_2$—C(O)—N(CH$_3$) (n-Butyl)
—O—(CH$_2$)$_4$—SO—CH$_2$—C(O)—N(CH$_3$)(n-Butyl)
—O—(CH$_2$)$_5$—S—CH$_2$—C(O)-N(CH$_3$)(n-Butyl), or
—O—(CH$_2$)$_5$—SO—CH$_2$—C(O)—N(CH$_3$)(n-Butyl).

11. Triphenylethylenes according to claim 1, selected from

{5-[4(1,2-Diphenyl-but-1-enyl)-phenoxy]-pentyl}-(4,4,5,5,5-pentafluoropentyl)-sulfide, {5-(4-(1,2-diphenyl-but-1-enyl)-phenoxy)-pentyl}-(4,4,5,5,5-pentafluoropentyl)-sulfoxide, {5-[4-1,2-diphenyl-but-1-enyl)-phenoxy]-pentyl}-(4,4,5,5,5-pentafluoropentyl)-sulfone, 4-(1-{4-[5-(4,4,5,5,5-pentafluoropentylsulfidyl)-pentyloxy]-phenyl}-2-phenyl-but-1-enyl)-phenol, 4-(1-{4-[5-(4,4,5,5,5-pentafluoropentanesulfinyl)-pentyloxy]-phenyl}-2-phenyl-but-1-enyl)-phenol, 4-((E,Z)-1-{4-[5-(4,4,5,5,5-pentafluoropentanesulfonyl)-pentyloxy]-phenyl}-2-phenyl-but-1-enyl)-phenol, (4,4,5,5,5-pentafluoropentyl)-{6-[4-((E,Z)-phenyl-1,2,3,4-tetrahydronaphth-1-ylidenemethyl)-phenoxy]-hexyl}-sulfoxide, (3-phenylprop-2-inyl)-{5-[4-((E,Z)-phenyl-1,2,3,4-tetrahydronaphth-1-ylidenemethyl)-phenoxy]-pentyl}-sulfoxide, (5-{4-[(E,Z)-1-(4-iodophenyl)-2-phenyl-but-1-enyl]-phenoxy}-pentyl)-(4,4,5,5,5-pentafluoropentyl)-sulfide, (5-{4-[(E,Z)-1-(4-iodophenyl)-2-phenyl-but-1-enyl]-phenoxy}-pentyl)-(4,4,5,5,5-pentafluoropentyl)-sulfoxide, 3-(1-{4-[5-(4,4,5,5,5-pentafluoropentylsulfidyl)-pentyloxy]-phenyl}-2-phenyl-but-1-enyl)-phenol, 3-((E,Z)-1-{4-[5-(4,4,5,5-pentafluoropentanesulfinyl)-pentyloxy]-phenyl}-2-phenyl-but-1-enyl)-phenol, (E,Z)-1-{4-[5-(4,4,5,5,5-pentafluoropentylsulfinyl)-pentyloxy]phenyl}-1-(4-hydroxyphenyl)-2-phenyl-but-1-ene, (E)-1-{4-[5-(4,4,5,5,5-pentafluoropentylsulfinyl)-pentyloxy]-phenyl}-1-(4-hydroxyphenyl)-2-phenyl-but-1-ene, {5-[4-(1,2-diphenyl-but-1(Z)-enyl)-phenoxy]-pentyl}-(4,4,5,5,5-pentafluoropentyl)-sulfoxide, {5-[4-(1,2-diphenyl-but-1(E)-enyl)-phenoxy]-pentyl}-(4,4,5,5,5-pentafluoropentyl)-sulfoxide, 4-(1-{4-[4-(4,4,5,5,5-pentafuoropentanesulfinyl)-butyloxy]-phenyl}-2-phenyl-but-1(E,Z)-enyl)-phenol, 4-(1-{4-[6-(4,4,5,5,5-pentafluoropentanesulfinyl)-hexyloxy]-phenyl}-2-phenyl-but-1(E,Z)-enyl)-phenol, 4-(1-{4-[(N-methyl-N-2-(4,4,5,5,5-pentafluoropentanesulfonyl)-ethyl-amino)-ethyloxy]-phenyl}-2-phenyl-but-1(E,Z)-enyl)-phenol, 4-(1-{4-[2-(N-methyl-N-2-(4,4,5,5,5-pentafluoropentanesulfinyl)-ethyl-amino)-ethyloxy]-phenyl}-2-phenyl-but-1(E,Z)-enyl)-phenol, (Z)-4-{12-(4,4,5,5,5-pentafluoropentylsulfinyl)-1-[4-(5-(4,4,5,5,5-pentafluoropentylsulfinyl)-pentyloxy)-phenyl]-2-phenyldodec-1-enyl}-phenol, (E)-4-{12-(4,4,5,5,5-pentafluoropentylsulfinyl)-1-[4-(5-(4,4,5,5,5-pentafluoropentylsulfinyl)-pentyloxy)-phenyl]-2-phenyldodec-1-enyl)}-phenol, N-butyl-2-(6-{4-[1-(4-hydroxy-phenyl)-2-phenyl-but-1(E,Z)-enyl]-phenoxy}-hexylthio)-N-methylacetamide, N-butyl-2-(6-{4-[1-(4-hydroxy-phenyl)-2-phenyl-but-1(E,Z)-enyl]-phenoxy}-hexanesulfinyl)-N-methylacetamide, N-butyl-2-(6-{4-[1-(4-hydroxy-phenyl)-2-phenyl-but-1(E,Z)-enyl]-phenoxy}-hexanesulfonyl)-N-methylacetamide, (Z)-4-{12-(4,4,5,5-pentafluoropentylsulfonyl)-1-[4-(5-(4,4,5,5-pentafluoropentylsulfonyl)-pentyloxy)-phenyl]-2-phenyldodec-1-enyl}-phenol, 4-(1-{4-[2-(4,4,5,5-pentafluoropentylthio)-ethyloxy]-phenyl}-2-phenyl-but-1(E,Z)-enyl)-phenol, 4-(1-{4-[2-(4,4,5,5-pentafluoropentylsulfinyl)-ethyloxy]-phenyl}-2-phenyl-but-1(E,Z)-enyl)-phenol, 4-(1-{4-[2-(N-methyl-N-3-(4,4,5,5-pentafluoropentylthio)-propyl-amino)-ethyloxy]-phenyl}-2-phenyl-but-1(E,Z)-enyl)-phenol, 4-(1-{4-[2-(4,4,5,5-pentafluoropentylsulfonyl)-ethyloxy]-phenyl}-2-phenyl-but-1(E,Z)-enyl)-phenol, 4-(1-{4-[2-(N-methyl-N-3-(4,4,5,5-pentafluoropentanesulfinyl)-propylamino-ethyloxy]-phenyl}-2-phenyl-but-1-(E,Z)-enyl)-phenol, 4-(1-{3-[4-(4,4,5,5-pentafluoropentylthio)-propyloxy]-phenyl}-2-phenyl-but-1(E,Z)-enyl)-phenol, 4-(1-{4-[3-(N-methyl-N-2-(4,4,5,5-pentafluoropentylthio)-ethyl-amino)-propyloxy]-phenyl}-2-phenyl-but-1(E,Z)-enyl)-phenol, 4-(1-{4-[3-(N-methyl-N-3-(4,4,5,5-pentafluoropentylthio)-propyl-amino)-propyloxy]-phenyl}-2-phenyl-but-1(E,Z)-enyl)-phenol, 4-(1-{4-[3-(4,4,5,5-pentafluoropentylsulfinyl)-propyloxy]-phenyl}-2-phenyl-but-1(E,Z)-enyl)-phenol, 4-(1-{4-[3-(N-methyl-N-2-(4,4,5,5-pentafluoropentanesulfinyl)-ethyl-amino)-propyloxy]-phenyl}-2-phenyl-but-1(E,Z)-enyl)-phenol or 4-(1-{4-[3-(N-methyl-N-3-(4,4,5,5-pentafluoropentanesulfinyl)-propylamino-propyloxy]-phenyl}-2-phenyl-but-1(E,Z)-enyl)-phenol.

12. A pharmaceutical preparation comprising an effective amount of a compound according to claim 1 and a pharmaceutically compatible vehicle.

13. A method of achieving an antiestrogenic effect comprising administering to a patient in need of such treatment an effective amount of a compound of claim 1.

14. A method of treating an estrogen-dependent disease comprising administering to a patient in need of such treatment an effective amount of a compound of claim 1.

* * * * *